United States Patent
Tani et al.

[11] Patent Number: 6,001,580
[45] Date of Patent: Dec. 14, 1999

[54] METHOD FOR ASSAYING ERK2 MAP KINASE

[75] Inventors: Akiyoshi Tani; Yuzo Ichimori, both of Osaka, Japan

[73] Assignee: Takeda Chemical Industries, Inc., Osaka, Japan

[21] Appl. No.: 08/622,277

[22] Filed: Mar. 27, 1996

[30] Foreign Application Priority Data

Mar. 28, 1995 [JP] Japan ................................. 7-070125
Nov. 24, 1995 [JP] Japan ................................. 7-305456
Dec. 8, 1995 [JP] Japan ................................. 7-320577

[51] Int. Cl.$^6$ ..................... G01N 33/53; G01N 33/574; A61K 39/395; C07K 16/00
[52] U.S. Cl. ................ 435/7.1; 424/139.1; 424/138.1; 435/7.23; 530/387.9; 530/387.7
[58] Field of Search ................................. 435/7.23, 7.1; 530/387.7, 387.9, 388.24; 424/138.1, 139.1

[56] References Cited

FOREIGN PATENT DOCUMENTS 8005632 12/1996 Japan .
WO 94/24159 10/1994 WIPO .

OTHER PUBLICATIONS

F. A. Gonzalez et al., Heterogeneous Expression of Four MAP Kinase Isoforms in Human Tissues, FEBS 304(2, 3):170–178 (1992).

J. Gomez–Cambronero et al., Granulocyte–Macrophage Colony–Stimulating Factor–Induced Protein Tyrosine Phosphorylation of Microtubule–Associated Protein Kinase in Human Neutrophils, Proc. Natl. Acad. Sci. 89:7551–7555 (1992).

S. J. Cook et al., RapV12 Antagonizes Ras–Dependent Activation of ERK1 and ERK2 by LPA and EGF in Rat–1 Fibroblasts, EMBO 12(9):3475–3485 (1993).

D. L. Charest et al., Molecular Cloning, Expression, and Characterization of the Human Mitogen–Activated Protein Kinase p44ERK1, Mol. Cell. Biol. 13(8):4679–4690 (1993).

M. G. Anderson et al., Requirement for Integration of Signals from two Distinct Phosphorylation Pathways for Activation of MAP Kinase, Nature 343:651–653 (1990).

F. Ito et al. Production of Various Anti MAP Kinase Antibodies, The Japanese Biochemical Society, 66(7):1068, Abstract 4887 (1994) (English translation attached).

Anti Mouse MAP Kinase (erk2), Monoclonal Antibody, Life Science Reagents 3rd ed., p. 737 (1995/1996) (English translation attached).

Campos–Gonzales et al, "Temperature–dependent tyrosine phoshorylation of microtubule–associated protein kinase in epidermal growth factor–stimulated human fibroblasts"Cell Regul. vol. 2, No. 8, pp. 663–674, Aug. 1991.

Affiniti Research Products Limited, "Data Sheet", 1994.

English Abstract of Japanese Publication No. 8–5632, 1996.

*Primary Examiner*—Yvonne Eyler
*Attorney, Agent, or Firm*—Finnegan, Henderson, Farabow, Garrett & Dunner, L.L.P.

[57] ABSTRACT

The monoclonal antibody generated by immunizing a mammal with human MAP kinase ERK1 and the polyclonal antibody generated by immunizing an animal with the phosphorylation region of the sequence of MAP kinase or a fragment of human MAP kinase are used either alone or in combination to detect and assay various MAP kinase species including ERK2.

14 Claims, 13 Drawing Sheets

PRIMER1   5' GGCATATGGCGGCGGCGGCGGCTCA 3'

PRIMER2   5' CCGGATCCGGCTAGGGGGCCTCCAGCAC 3'

① PEPTIDE-1
② PEPTIDE-2
③ PEPTIDE-3
④ PEPTIDE-4

1: IgG BEFORE PURIFICATION

2: FRACTION WHICH BINDS TO IMMUNIZED PEPTIDE

3: FRACTION WHICH BINDS TO IMMUNIZED PEPTIDE AND WHICH DOES NOT BIND TO PHOSPHORYLATED TYROSINE

```
  1 MAAAAAAGAG  PEMVRGQVFD  VGPRYTNLSY  IGEGAYGMVC  SAYDNVNKVR
 51 VAIKKISPFE  HQTYCQRTLR  EIKILLRFRH  ENIIGINDII  RAPTIEQMKD
101 VYIVQDLMET  DLYKLLKTQH  LSNDHICYFL  YQILRGLKYI  HSANVLHRDL
151 KPSNLLLNTT  CDLKICDFGL  ARVADPDHDH  TGFLTEYVAT  RWYRAPEIML
201 NSKGYTKSID  IWSVGCILAE  MLSNRPIFPG  KHYLDQLNHI  LGILGSPSQE
251 DLNCIINLKA  RNYLLSLPHK  NKVPWNRLFP  NADSKALDLL  DKMLTFNPHK
                    ⑤                              ⑥
301 RIEVEQALAH  PYLEQYYDPS  DEPIAEAPFK  FDMELDDLPK  EKLKELIFEE
351 TARFQPGYRS
```

⑤ PEPTIDE-5        ⑥ PEPTIDE-6

*FIG. 11*

SOLID PHASE: ANTIBODY AGAINST PEPTIDE-3

—□— INACTIVE-FORM ERK1
—◇— ACTIVE-FORM ERK1
—○— INACTIVE-FORM ERK2
—△— ACITVE-FORM ERK2

SOLID PHASE: ANTIBODY AGAINST PEPTIDE-6

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

His Thr Gly Phe Leu Thr Glu Tyr Val Ala Thr Arg
1             5                    10

(2) INFORMATION FOR SEQ ID NO:2:

(i) SEQUENCE CHARACTERISTICS:
      (A) LENGTH: 19 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Cys Ser Leu Pro Ser Lys Thr Lys Val Ala Trp Ala Lys Leu Phe Pro
1               5                   10                  15

Lys Ser Asp (2) INFORMATION FOR SEQ ID NO:3:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Cys Ile Phe Gln Glu Thr Ala Arg Phe Gln Pro Gly Val Leu Glu Ala
1               5                   10                  15

Pro (2) INFORMATION FOR SEQ ID NO:4:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Cys Ser Leu Pro His Lys Asn Lys Val Pro Trp Asn Arg Leu Phe Pro
1               5                   10                  15

Asn Ala Asp (2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Cys Ile Phe Glu Glu Thr Ala Arg Phe Gln Pro Gly Tyr Arg Ser
1               5                   10                  15

(2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Cys Glu His Asp His Thr Gly Phe Leu Thr Glu Tyr Val Ala Thr Arg
1               5                   10                  15

Trp

-continued (2) INFORMATION FOR SEQ ID NO:7:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Ile Phe Gln Glu Thr Ala Arg Phe Gln Pro Gly Val Leu Glu Ala Pro
1               5                   10                  15
```

(2) INFORMATION FOR SEQ ID NO:8:

(i) SEQUENCE CHARACTERISTICS:
        (A) LENGTH: 379 amino acids
        (B) TYPE: amino acid
        (C) STRANDEDNESS: single
        (D) TOPOLOGY: linear (ii) MOLECULE TYPE:

(xi) SEQUENCE DESCRIPTION: SEQ ID NO:8:

```
Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
                20                  25                  30

Gly Gln Pro Phe Asp Val Gly Pro Arg Tyr Thr Gln Leu Gln Tyr Ile
                35                  40                      45

Gly Glu Gly Ala Tyr Gly Met Val Ser Ser Ala Tyr Asp His Val Arg
            50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
                100                 105                 110

Glu Ala Met Arg Asp Val Tyr Ile Val Gln Asp Leu Met Glu Thr Asp
                115                 120                 125

Leu Tyr Lys Leu Leu Lys Ser Gln Gln Leu Ser Asn Asp His Ile Cys
            130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
                180                 185                 190

Pro Glu His Asp His Thr Gly Phe Leu Thr Glu Tyr Val Ala Thr Arg
                195                 200                 205

Trp Tyr Arg Ala Pro Glu Ile Met Leu Asn Ser Lys Gly Tyr Thr Lys
210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
```

```
                    275                 280                 285
Lys Val Ala Trp Ala Lys Leu Phe Pro Lys Ser Asp Ser Lys Ala Leu
    290                 295                 300

Asp Leu Leu Asp Arg Met Leu Thr Phe Asn Pro Asn Lys Arg Ile Thr
305                 310                 315                 320

Val Ala Ala Ala Leu Ala His Pro Tyr Leu Glu Gln Tyr Tyr Asp Pro
                325                 330                 335

Thr Asp Glu Pro Val Ala Glu Glu Pro Phe Thr Phe Ala Met Glu Leu
                340                 345                 350

Asp Asp Leu Pro Lys Glu Arg Leu Lys Glu Leu Ile Phe Gln Glu Thr
                355                 360                 365

Ala Arg Phe Gln Pro Gly Val Leu Glu Ala Pro
370                 375
```

(2) INFORMATION FOR SEQ ID NO:9:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Gly Met Val Ser Ser Ala Tyr Asp His Val Arg Lys Thr Arg Val Ala
1               5                   10                  15

Ile Lys
```

(2) INFORMATION FOR SEQ ID NO:10:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Glu His Asp His Thr Gly Phe Leu Thr Glu Tyr Val Ala Thr Arg Trp
1               5                   10                  15
```

(2) INFORMATION FOR SEQ ID NO:11:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Ser Leu Pro Ser Lys Thr Lys Val Ala Trp Ala Lys Leu Phe Pro Lys
1               5                   10                  15

Ser Asp
```

(2) INFORMATION FOR SEQ ID NO:12:

(i) SEQUENCE CHARACTERISTICS:
        (A) LENGTH: 16 amino acids
        (B) TYPE: amino acid
        (C) STRANDEDNESS: single
        (D) TOPOLOGY: linear

```
    (ii) MOLECULE TYPE: peptide (xi) SEQUENCE DESCRIPTION: SEQ ID NO:12:

Ile Phe Gln Glu Thr Ala Arg Phe Gln Pro Gly Val Leu Glu Ala Pro
1               5                   10                  15

(2) INFORMATION FOR SEQ ID NO:13:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Cys Gly Met Val Ser Ser Ala Tyr Asp His Val Arg Lys Thr Arg Val
1               5                   10                  15

Ala Ile Lys (2) INFORMATION FOR SEQ ID NO:14:

(i) SEQUENCE CHARACTERISTICS:
        (A) LENGTH: 360 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
                20                  25                  30

Glu Gly Ala Tyr Gly Met Val Cys Ser Ala Tyr Asp Asn Val Asn Lys
            35                  40                  45

Val Arg Val Ala Ile Lys Lys Ile Ser Pro Phe Glu His Gln Thr Tyr
        50                  55                  60

Cys Gln Arg Thr Leu Arg Glu Ile Lys Ile Leu Leu Arg Phe Arg His
65              70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
    130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Pro His Thr Gly Phe Leu Thr Glu Tyr Val Ala Thr Arg Trp
            180                 185                 190

Tyr Arg Ala Pro Glu Ile Met Leu Asn Ser Lys Gly Tyr Thr Lys Ser
        195                 200                 205

Ile Asp Ile Trp Ser Val Gly Cys Ile Leu Ala Glu Met Leu Ser Asn
    210                 215                 220
```

```
Arg Pro Ile Phe Pro Gly Lys His Tyr Leu Asp Gln Ile Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
        275                 280                 285

Leu Leu Asp Lys Met Leu Thr Phe Asn Pro His Lys Arg Ile Glu Val
    290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
            340                 345                 350

Arg Phe Gln Pro Gly Tyr Arg Ser
            355                 360

(2) INFORMATION FOR SEQ ID NO:15:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Ser Leu Pro His Lys Asn Lys Val Pro Trp Asn Arg Leu Phe Pro Asn
1               5                   10                  15

Ala Asp (2) INFORMATION FOR SEQ ID NO:16:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Ile Phe Glu Glu Thr Ala Arg Phe Gln Pro Gly Tyr Arg Ser
1               5                   10

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GGCATATGGC GGCGGCGGCG GCTCA                                           25

(2) INFORMATION FOR SEQ ID NO:18:
```

-continued

```
    (i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CCGGATCCGG CTAGGGGGCC TCCAGCAC                                          28
```

METHOD FOR ASSAYING ERK2 MAP KINASE

FIELD OF THE INVENTION

The present invention relates to the assay of MAP kinase and active-form MAP kinase using an antibody. More particularly, the invention relates to a monoclonal antibody binding to human MAP kinase ERK1, a method of producing the same antibody, an antibody binding to active-form MAP kinase, a method of producing the antibody, a polyclonal antibody binding to MAP kinase species [MAP kinase EPK1, MAP kinase ERK2, and active-form MAP kinase], and uses for said respective antibodies, namely detection and assay systems for MAP kinase or active-form MAP kinase using said antibodies.

BACKGROUND OF THE INVENTION

Mitogen-activated protein kinase (MAP kinase) was first identified as a protein phosphorylase which is activated when a growth factor is added to cultured cells (Proc. Natl. Acad. Sci. USA, 84, 1502–1506, 1987). However, subsequent research revealed that this enzyme is involved in various vital phenomena such as neuronal differentiation (J. Biol. Chem., 265, 4730–4735, 1990), activation of immune cells (J. Immunol., 144, 2683–2689, 1990) and secretions (J. Cell Biol., 110, 731–742, 1990). As regards human MAP kinase, cloning of its gene showed the existence of several molecular species of high homology but the main species are two, namely ERK1 and ERK2. These two proteins are highly homologous (84.7%) (FEBS LETT., 304, 170–178, 1992). Though their functional dissimilarity had been presumed for some time, no difference in vitro, whether in function or in activity, has been discovered to this day.

Several kinds of antibodies against this MAP kinase have been obtained but the majority of them are polyclonal antibodies. In this connection, several monoclonal antibodies are known. Among them are Clone MK12 [Julian Gomez-Cambronero et al., Proc. Natl. Acad. Sci. USA, 89, 7551–7555, 1992] or [Seikagaku Kogyo Catalog (1993/94), p.184] and Clone B9 [UBI Catalog (1993), p.33]. However, there is no report on monoclonal antibodies that would ever distinguish between ERK1 and ERK2. There is not a case, either, in which a monoclonal antibody was ever obtained by immunizing an animal other than man (e.g. mice) with human MAP kinase.

So far, as antibodies capable of distinguishing between ERK1 and ERK2, Simon J. Cook and coworkers have reported polyclonal antibodies specifically binding to these proteins, respectively [EMBO Journal, 12, 3475–3485, 1993] but these antibodies were invariably used in Western blotting and immunoprecipitation only and quantitation of MAP kinase protein has not been done with them.

MAP kinase is a serine-threonine kinase which is activated when both the Thr and Tyr residues in the Thr-Glu-Tyr sequence are phosphorylated and phosphorylation of these two residues are considered to be necessary and sufficient conditions for activation [Neil G. Anderson et al., Nature, 343, 651–653, 1990]. The antibody reported by Ito et al. [Proceedings of 1994 Congress of Japanese Biochemical Society, Lecture No. 4887] and the New England Biolabs antibody are known as antibodies that specifically bind to phosphorylated MAP kinase. However, these are used only in the Western blotting and immunoprecipitation of active-form MAP kinase and immune staining of cells.

No quantitative determination of active-form MAP kinase has been attempted.

So far, as methods for assay of MAP kinase activity, the technique comprising phosphorylating myelin basic protein (MBP) with $\gamma\text{-}^{32}\text{P-ATP}$ and measuring the radioactivity taken up in the MBP [Ahn, N. et al., J. Biol. Chem., 266, 4220–4227, 1991] and the technique comprising subjecting a cell extract to SDS-PAGE and phosphorylating MBP within the gel [Leevers, S. J. et al., EMBO Journal, 11, 569–574, 1992] are mainly used in practice but these techniques have the drawback that a radioisotope must be employed. As a comparatively expedient method, a technique utilizing the difference in electrophoretic mobility between the active-form and the inactive-form is known [e.g. Johan Van Lint et al., Molecular and Cellular Biochemistry, 127/128, 171–178, 1993] but assays can hardly be done by this technique.

BRIEF EXPLANATION OF THE DRAWINGS

FIG. 6 shows the amino acid sequence of human MAP kinase ERK1 (SEQ ID NO:8) and the amino acid sequences of the four kinds of synthetic peptides used in Example 3 Peptide 1 corresponds to SEQ ID NO:9, peptide 2 corresponds to SEQ ID NO:10, peptide 3 corresponds to SEQ ID NO:11 and peptide 4 corresponds to SEQ ID NO:12.

FIG. 11 shows the sequence for human ERK2 (SEQ ID NO:14) and the sequences of the synthetic peptides used in Example 9 Peptide 5 corresponds to SEQ ID NO:15 and peptide 6 corresponds to SEQ ID NO:16.

SUMMARY OF THE INVENTION

Figures 1, 2:
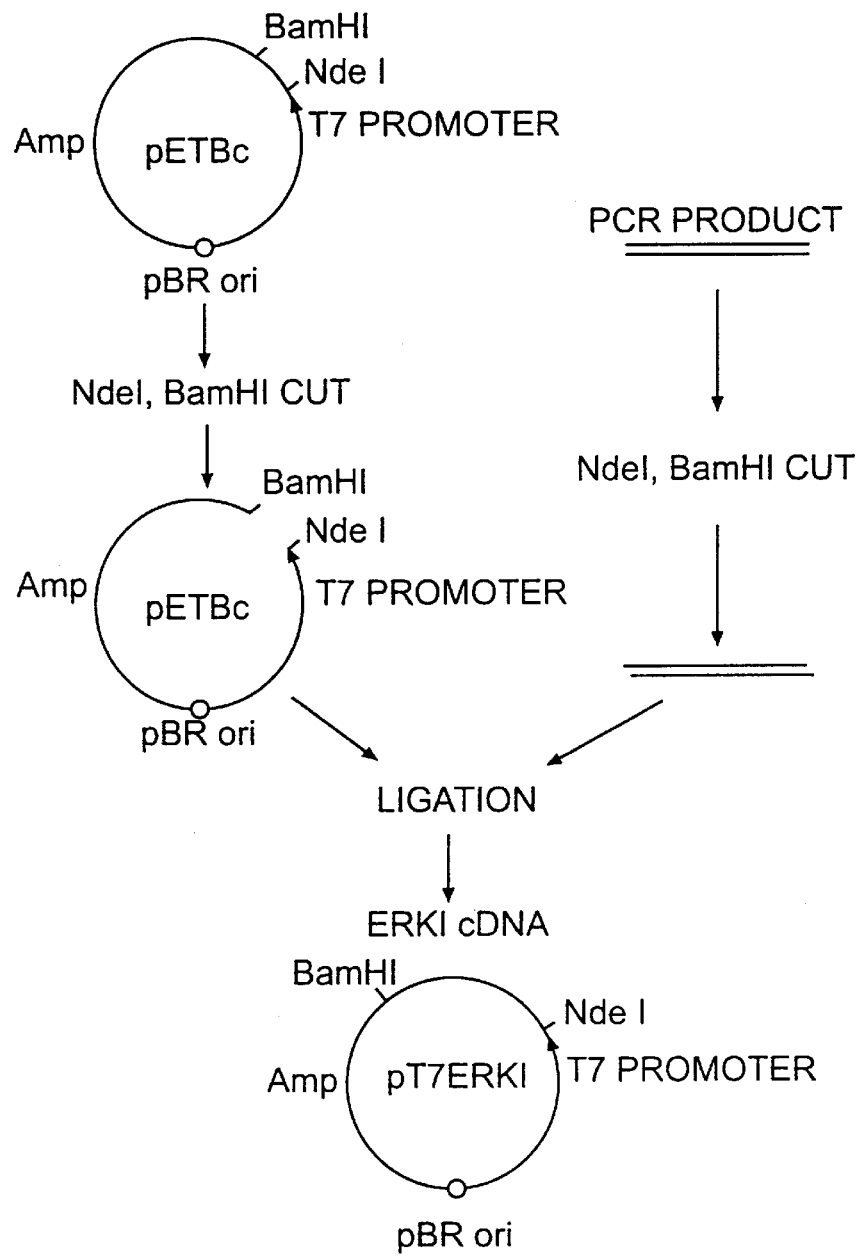
FIG. 1 shows the base sequences of the primers used in the PCR amplification of human MAP kinase ERK1 cDNA Primer 1 corresponds to SEQ ID NO:17 and Primer 2 corresponds to SEQ ID NO:18.
FIG. 2 shows the procedure of constructing a plasmid DNA for use in the inductive synthesis of human MAP kinase ERK1 protein in *E coli*.

The inventors recognize that if monoclonal antibodies and polyclonal antibodies that specifically bind to various types of MAP kinase derived from a variety of animal species or of various molecular species, either in active-form or in inactive-form, with high sensitivity could be constructed, it should become possible to ascertain the distribution of each kinase, the level of its expression, and change in its phosphorylase activity in various cells or tissues and, hence, obtain further insight into the role of MAP kinase in vivo.

Furthermore, the inventors recognized that if an antibody binding to phosphorylated MAP kinase with high sensitivity could be constructed, the activity of MAP kinase could be detected or assayed by the usual enzyme immunoassay or Western blotting method.

In addition, by using such antibodies in combination, it would become possible to assay ERK1 and ERK2 activities independently of each other and in a sandwich enzyme immunoassay system so that the role of MAP kinase in vivo, for instance, and even the different roles played by ERK1 and ERK2 could be elucidated more easily than ever before.

Also, it was recognized by the inventors that simple determination of MAP kinase content and/or activity would facilitate the diagnosis of various MAP kinase-related diseases and the analysis of mechanism of drug action.

The inventors of the present invention, using human MAP kinase ERK1 (a species of MAP kinase) as an immunogen, succeeded in obtaining a monoclonal antibody having a specific binding affinity for this particular protein. This monoclonal antibody binds neither human MAP kinase ERK2 nor rat MAP kinase ERK1. Therefore, when used in immunochemical assays, the monoclonal antibody of the invention is able to detect or assay human cellular MAP kinase ERK1 with high specificity and sensitivity. Moreover, by using this monoclonal antibody, human MAP kinase ERK1 can be purified from human cells, for instance, with good efficiency. Further, using a peptide (synthetic peptide) synthesized by phosphorylating the amino acid sequence corresponding to the phosphorylation region of MAP kinase as an immunogen, the inventors succeeded in obtaining an antibody having a specific binding affinity for active-form MAP kinase. This antibody does not bind to inactive-form MAP kinase and, therefore, when used in immunochemical assays, it is able to detect or assay active-form human, rat, mouse or other animal MAP kinase with high specificity and high sensitivity, without regard to whether the kinase is ERK1 or ERK2. In addition, by using this antibody, active-form MAP kinase can be purified with good efficiency. Those findings were followed by further research, which has resulted in the development of the present invention herein disclosed.

The present invention, therefore, is directed to:
(1) An IgG type monoclonal antibody generated by using human MAP kinase ERK1 as an immunogen and capable of binding to human MAP kinase ERK1.
(2) A monoclonal antibody capable of binding to human MAP kinase ERK1 but incapable of binding to human MAP kinase ERK2, rat MAP kinase ERK1 or rat MAP kinase ERK2.
(3) A cloned hybridoma fusion-derived from splenocytes of a mammal immunized with human MAP kinase ERK1 and homologous or heterologous lymphoid cells.
(4) A method for producing the hybridoma (3) which comprises subjecting splenocytes of a mammal immunized with human MAP kinase ERK1 and homologous or heterologous lymphoid cells to cell fusion, followed by cloning.
(5) A method for producing the monoclonal antibody (1) or (2) which comprises growing the hybridoma of (3) in a liquid medium or in the peritoneal cavity of a mammal.
(6) A method of detecting or assaying human MAP kinase ERK1 which comprises using the monoclonal antibody (1) or (2).
(7) The method (6) for detecting or assaying human MAP kinase ERK1, said method being an enzyme immunoassay method.
(8) A method of assaying human MAP kinase ERK1 activity which comprises using the monoclonal antibody (1) or (2).
(9) A method of purifying human MAP kinase ERK1 which comprises using the monoclonal antibody (1) or (2).
(10) An anti-MAP kinase antibody capable of specifically binding to a peptide having the sequence His-Thr-Gly-Phe-Leu-(Thr-PO$_3$H$_2$)-Glu-(Tyr-PO$_3$H$_2$)-Val-Ala-Thr-Arg (SEQ ID NO:1).
(11) A method of detecting or assaying active-form MAP kinase which comprises using the antibody (10).
(12) The method (11) for detecting or assaying active-form MAP kinase, said method being an enzyme immunoassay method.
(13) A method of purifying active-form MAP kinase which comprises using the antibody (10).
(14) A method of detecting or assaying active-form human MAP kinase ERK1 which comprises using the monoclonal antibody (1) or (2) and the antibody (10).
(15) The method (14) for detecting or assaying active-form human MAP kinase ERK1, said method being an enzyme immunoassay method.

Using peptides having the amino acid sequences of MAP kinase ERK1 and ERK2, respectively, as the immunogen, the inventors of the present invention succeeded also in constructing antibodies each having a specific binding affinity for the corresponding MAP kinase. The anti-ERK1 antibody binds to human and rat ERK1 molecules but to neither human ERK2 nor rat ERK2. On the other hand, the anti-ERK2 antibody binds to both human and rat ERK2 molecules but to neither human nor rat ERK1. Therefore, with these antibodies, each of MAP kinase ERK1 and ERK2 can be immunochemically detected or assayed independently of the other.

Furthermore, using a synthetic peptide (phosphorylated peptide) having the amino acid sequence corresponding to the phosphorylation region of MAP kinase as the immunogen, the inventors succeeded in obtaining an antibody having a specific binding affinity for active-form MAP kinase. While this antibody is specifically binding to active-form human and rat MAP kinase (both ERK1 and ERK2), it does not bind inactive-form MAP kinase or other phosphate group-containing proteins. Therefore, by carrying out an immunochemical assay using this antibody, the active-form MAP kinase can be detected or assayed with high specificity and sensitivity as mentioned above. Moreover, by using it in combination with the antibody which binds either ERK1 or ERK2 specifically, either one of active-form ERK1 and active-form ERK2 can be independently detected or assayed to the exclusion of the other.

Based on the above findings, the inventors did further research and elaborated the invention as herein disclosed.

The present invention, therefore, is further directed to:

(16) An anti-MAP kinase antibody capable of specifically binding to a peptide having the sequence Ser-Leu-Pro-Ser-Lys-Thr-Lys-Val-Ala-Trp-Ala-Lys-Leu-Phe-Pro-Lys-Ser-Asp (SEQ ID NO:11, peptide (3)).

(17) An anti-MAP kinase antibody capable of specifically binding to a peptide having the sequence Ile-Phe-Gln-Glu-Thr-Ala-Arg-Phe-Gln-Pro-Gly-Val-Leu-Glu-Ala-Pro (SEQ ID NO:12, peptide (4))

(18) An anti-MAP kinase antibody capable of specifically binding to a peptide having the sequence Ser-Leu-Pro-His-Lys-Asn-Lys-Val-Pro-Trp-Asn-Arg-Leu-Phe-Pro-Asn-Ala-Asp (SEQ ID NO:15, peptide (5)).

(19) An anti-MAP kinase antibody capable of specifically binding to a peptide having the sequence Ile-Phe-Glu-Glu-Thr-Ala-Arg-Phe-Gln-Pro-Gly-Tyr-Arg-Ser (SEQ ID NO:16, peptide (6)).

(20) An anti-MAP kinase antibody capable of specifically binding to a peptide having the sequence Glu-His-Asp-His-Thr-Gly-Phe-Leu-Thr-Glu-Tyr-Val-Ala-Thr-Arg-Trp (SEQ ID NO:10, peptide (2)).

(21) A method of assaying MAP kinase which comprises using an antibody capable of specifically binding to MAP kinase, to a mutein derived from MAP kinase, or to a fragment of MAP kinase.

(22) The method (21) for assaying MAP kinase, wherein the antibody is the antibody (16), (17), (18), (19) or (20).

(23) The method (21) or (22) for assaying MAP kinase, said method being an enzyme immunoassay method.

(24) The method (23) for assaying MAP kinase, said method being carried out by the sandwich technique.

(25) The method (21), (22), (23) or (24) for assaying MAP kinase, wherein the MAP kinase is ERK1.

(26) The method (25) for assaying MAP kinase ERK1, wherein the antibody of (16), (17) or (20) is used.

(27) The method (21), (22), (23) or (24) for assaying MAP kinase, wherein the MAP kinase is ERK2.

(28) The method (27) for assaying MAP kinase ERK2, wherein the antibody (18) or (19) is used.

(29) The method (21), (22), (23) or (24) for assaying MAP kinase, wherein the MAP kinase is active-form ERK1.

(30) The method (29) for assaying active-form MAP kinase ERK1, wherein the antibody (9) and the antibody (16), (17) or (20) are used.

(31) The method (21), (22), (23) or (24) for assaying MAP kinase, wherein the MAP kinase is active-form ERK2.

(32) The method (31) for assaying active-form MAP kinase ERK2, wherein the antibody (9) and the antibody (18) or (19) are used.

DETAILED DESCRIPTION OF THE INVENTION

The MAP kinase (ERK1 or ERK2), such as human MAP kinase ERK1, which is used for immunizing a mammal in accordance with the present invention can be any MAP kinase (ERK1 or ERK2) of mammalian cell origin or molecular species, whether it is the native enzyme or a fragment thereof or a mutein thereof. For example, a MAP kinase (ERK1 or ERK2) of human cell origin can be purified from EGF-stimulated-A431 cells by the procedure taught by Bryan Ray and coworkers [J. Biol. Chem., 263, 12721–12727]. For use as the immunogen, the MAP kinase mentioned above can be isolated from a tissue or cells or can be harvested on an industrial scale by constructing an expression vector containing a DNA having the nucleotide sequence coding for the MAP kinase and introducing it into suitable host cells. The expression vector can be produced typically by the following procedure.

(a) Isolate the RNA coding for MAP kinase.

(b) From this RNA, synthesize a single-stranded complementary DNA (cDNA) and, then, a double-stranded DNA.

(c) Insert the complementary DNA into a plasmid.

(d) Transform a host with the resulting recombinant plasmid.

(e) Grow the transformant and isolate the plasmid containing the objective DNA from the transformant by a suitable procedure such as the colony hybridization method using a DNA probe.

(f) Cut out the objective cloned DNA from said plasmid.

(g) Insert this cloned DNA downstream of the promoter of a vector.

By introducing the expression vector thus obtained into a suitable host (e.g. *Escherichia coli, Bacillus subtilis*, yeasts, or animal cells) and growing the resulting transformant in a medium, MAP kinase (ERK1 or ERK2), typically human MAP kinase ERK1, can be produced. The MAP kinase protein mentioned above includes MAP kinase muteins as well. A MAP kinase mutein is inherently the result of mutation of the amino acid sequence of an original peptide or protein, typically as induced by addition, deletion and/or substitution of amino acids.

The addition of amino acids means the addition of at least one amino acid.

The deletion of amino acids means the deletion of at least one of the constituent amino acids of MAP kinase.

The substitution of other amino acids means the substitution of at least one different amino acid for one of the constituent amino acids of the MAP kinase.

The addition of amino acids in the context of a MAP kinase mutein does not include the addition of methionine derived from the initiation codon or the signal peptide as used in the peptide expression. While the number of amino acids added is at least one, there is no limitation on the number of additions unless the characteristics of the parent MAP kinase are lost. The preferred is a fragment or the entire of the amino acid sequence which has been established to have high homology between various MAP-kinases.

The number of constituent amino acids deleted in an MAP kinase mutein with such deletion is at least one amino acid and the upper limit of the number of amino acid deletion is up to the point where the deletions result in the loss of the characteristics of the parent MAP kinase.

In a MAP kinase mutein involving substitution of amino acids, the number of constituent amino acids (amino acids to be replaced) of the parent MAP kinase is at least 1 but the upper limit of the number of substitutions is up to the point where the characteristics of the parent MAP kinase are lost.

The candidate constituent amino acid (the amino acid to be replaced) may be any amino acid inclusive of cysteine, and cysteine is the preferred candidate for substitution. The amino acid other than cysteine that may be replaced includes aspartic acid, arginine, glycine, valine, or any other amino acid.

When the amino acid to be replaced is cysteine, the substitute amino acid (the amino acid used for substitution)

is preferably a neutral amino acid. The neutral amino acid that can be used includes but is not limited to glycine, valine, alanine, leucine, isoleucine, tyrosine, phenylalanine, histidine, tryptophan, serine, threonine, and methionine. Particularly preferred are serine and threonine.

In case the amino acid to be replaced is any amino acid other than cysteine, the substitute amino acid is typically an amino acid differing from the amino acid to be replaced in hydrophilicity/hydrophobicity or in electric charge. Where the amino acid to be replaced is aspartic acid, for instance, the substitute amino acid may, for example, be asparagine, threonine, valine, phenylalanine or arginine. Particularly preferred is asparagine or arginine.

When the amino acid to be replaced is arginine, the candidate substitute amino acid includes glutamine, threonine, leucine, phenylalanine, aspartic acid, etc., although glutamine is particularly preferred.

When the amino acid to be replaced is glycine, the candidate substitute amino acid includes but is not limited to threonine, leucine, phenylalanine, serine, glutamic acid, arginine, etc., although threonine is particularly preferred.

When the amino acid to be replaced is serine, the candidate substitute amino acid includes but is not limited to methionine, alanine, leucine, cysteine, glutamine, arginine, aspartic acid, etc. Particularly preferred is methionine.

When the amino acid to be replaced is valine, the candidate substitute amino acid includes but is not limited to serine, leucine, proline, glycine, lysine, aspartic acid, etc. Among them, serine is particularly preferred.

The preferred amino acids to be replaced are aspartic acid, arginine, glycine, serine, and valine. The preferred substitute amino acids are asparagine, glutamine, arginine, threonine, methionine, serine, and leucine.

The above-mentioned substitution may involve two or more substitutions. Particularly preferred are muteins representing the substitution of 2 or 3 constituent amino acids.

The above mutein may represent a combination of any two or three of the addition, deletion, and substitution described above. For the production of such a mutein, the site-directed mutagenesis technique is employed. This well-known technique is described in Lather, R. F. and Lecoq, J. P., Genetic Engineering, pp. 31–50, Academic Press, 1983. The oligonucleotide-directed mutagenesis technique is described in Smith, M. and Gillam, S., Genetic Engineering, Principles and Methods, Vol. 3, pp. 1–32, Prenam Press, 1981.

The structural gene coding for the mutein can be produced typically by the following procedure.

(a) Hybridize a single-stranded DNA comprising the single-stranded DNA chain of the structural gene of MAP kinase with a mutant oligonucleotide primer (this primer must be complementary to the cysteine codon to be replaced or, in some cases, a region including the antisense triplet pairing with the codon. However, disagreement with other amino acid encoding codons or, in certain cases, the antisense triplet is acceptable).

(b) Extend the primer with DNA polymerase to produce a mutagenic heteroduplex.

(c) Replicate this mutagenic heteroduplex.

Then, the phage DNA transporting the mutated gene is isolated and introduced into a plasmid.

The plasmid thus obtained is used to transform a suitable host and the resulting transformant is grown in a medium so as to produce the desired mutein.

The mutein representing a deletion of any constituent amino acid of MAP kinase for use as the immunogen in the practice of the present invention is preferably a mutein containing not less than 100 amino acid residues of the sequence of the parent MAP kinase. Still more preferred is a mutein containing not less than 110 amino acid residues.

A monoclonal antibody against MAP kinase such as human MAP kinase ERK1, human MAP kinase ERK2, etc. can be produced by immunizing a mammal with the MAP kinase, a mutein thereof, or a fragment peptide thereof, subjecting harvested spleen cells to cell fusion with mammalian lymphoid cells, and carrying out cloning of the resulting hybridoma. In using said MAP kinase, mutein or fragment peptide for immunization, the MAP kinase may be coupled to a carrier protein in the first place and the resulting complex be used as the immunogen. The carrier protein that can be used includes but is not limited to bovine serum albumin, bovine thyroglobulin, and hemocyanin.

When a carrier protein complex is used, the coupling ratio of carrier protein to MAP kinase (by weight) is about 0.1 through 30/1. The preferred ratio is about 0.5–5/1.

For the coupling reaction between hapten and carrier, a variety of condensing agents can be employed, although the use of glutaraldehyde or a carbodiimide reagent is particularly preferred.

The mammal that can be immunized with MAP kinase, e.g. human MAP kinase ERK1, or a complex thereof includes various experimental animals such as sheep, goat, rabbit, guinea pig, rat, mouse, etc. For the production of a monoclonal antibody, however, the use of rats or mice is preferred. For immunizing a mouse, for instance, any of the intraperitoneal, intravenous, intramuscular, intradermal and subcutaneous routes can be employed. It is, however, generally preferable to choose the subcutaneous, intraperitoneal or intravenous route. Most desirable is the subcutaneous route. The inoculation interval, immunizing dose and other parameters can be optimized by routine experimentation known to those of skill in the art. A typical routine procedure comprises immunizing the host twice to about six times at intervals of 2 weeks and excise the spleen about 1–5 days, preferably about 2–4 days, after the last immunization for harvesting spleen cells. The inoculum size is not less than about 0.1 $\mu$g peptide/mouse/dose and preferably about 10 $\mu$g–300 $\mu$g/mouse/dose. A recommended protocol suggests performing blood sampling prior to isolation of the spleen and confirming a sufficient elevation of the blood antibody titer before subjecting the spleen cells to cell fusion.

The cell fusion mentioned above is typically carried out between the mouse spleen cell and a lymphoid cell line such as a homologous or heterologous (preferably homologous) myeloma cell line carrying a suitable marker such as hypoxanthine-guanine phosphoribosyl transferase deficiency (HGPRT$^-$) or thymidine kinase deficiency (TK$^-$) [e.g. P3-X63-Ag·8U1, Ichimori et al., Journal of Immunological Methods, 80, 55, 1985]. Typically the method of Kohler and Milstein [Nature, 256, 495, 1975] is used for this cell fusion. Thus, for example, myeloma cells and spleen cells in a ratio of about 1:5 are suspended in e.g. a 1:1 mixture of Iscove's medium and HAM F-12 medium (hereinafter referred to as IH medium) and fused with the aid of a fusion promoter such as Sendai virus or polyethylene glycol (PEG). Of course, other fusion promoters such as dimethyl sulfoxide (DMSO) can be added as alternatives. Generally the average molecular weight of PEG used for this purpose is about 1000–9000, the reaction time is about 0.5–30 minutes, and the concentration is about 10–80%, for instance. To mention a preferred protocol, cell fusion can be efficiently accomplished using about 35–55% PEG 6000 in about 4–10 minutes. The fused cell can be selectively expanded in a medium such as hypoxanthine-aminopterin-thymidine medium [HAT medium; Nature, 256, 495, 1975].

The culture supernatants of grown cells are screened for productivity of the objective antibody. This screening for antibody titer can be carried out in the following manner. As a first step, the production of an antibody reactive against the antigen peptide used for immunization is checked. While this examination can be made by radioimmunoassay (RIA) or enzyme immunoassay (EIA), each of these techniques is open to a variety of modifications. A typical EIA procedure is described below. The rabbit anti-mouse immunoglobulin antibody, for instance, is coupled to a solid phase such as cellulose beads beforehand in the conventional manner. This antibody-coupled solid phase is added to the culture supernatant to be analyzed or mouse serum and allowed to react at a constant temperature (about 4–40° C.; the same applies hereinafter) for a given time. The reaction product is then rinsed thoroughly and the enzyme-labeled antigen peptide (an enzyme and the antigen peptide coupled and purified in the routine manner) is added and allowed to react at a constant temperature for a given time. After the reaction product is rinsed thoroughly, a substrate for the enzyme is added and the reaction is carried out at a constant temperature for a given time. Then, the colored reaction product is quantitated on the basis of absorbance or the intensity of fluorescence.

The wells containing cells showing growth in a screening medium and exhibiting antibody activity against the antigen peptide used for immunization are selected and these cells are preferably cloned by the limiting dilution method or the like. The supernatant of the cloned cells is subjected to the same screening as above and the cells in wells showing high antibody titers are expanded whereby a monoclonal antibody-producing hybridoma clone reactive to the same antigenic peptide as used for immunization is obtained.

This cloned hybridoma is expanded in a liquid medium. Typically, the cloned hybridoma is cultured in a liquid medium, such as RPMI-1640 [Moore, G. E. et al., Journal of American Medical Association, 199, 549, 1967] supplemented with about 0.1–40% of bovine serum, for about 2–10 days, preferably about 3–5 days. In this manner, the objective monoclonal antibody can be harvested from the culture fluid. As an alternative, the antibody can be obtained by inoculating a mammal intraperitonally with the hybridoma, allowing the cells to grow in situ, and collecting the ascites. For this purpose, assuming that the mouse is used as said mammal, typically BALB/c mice pretreated with mineral oil or the like are inoculated intraperitoneally with about $1 \times 10^4$–$1 \times 10^7$ cells, preferably about $5 \times 10^5$–$2 \times 10^6$ cells, of the hybridoma and after about 7–20 days, preferably about 10–14 days, the ascites fluid is harvested. The antibody secreted and accumulated in the ascites fluid is subjected to a purification procedure such as ammonium sulfate fractionation, DEAE-cellulose column chromatography or the like, whereby the objective monoclonal antibody can be easily isolated as a pure immunoglobulin.

In this manner, the monoclonal antibody to MAP kinase such as human MAP kinase ERK1 can be obtained.

The preferred monoclonal antibody is a monoclonal antibody which recognizes a region of difference in amino acid sequence typically between human MAP kinase ERK1 and human MAP kinase ERK2 or between human MAP kinase ERK1 and non-human (e.g. rat) MAP kinase ERK1. Particularly preferred is a monoclonal antibody, such as HE113, which recognizes the C-terminal amino acid sequence containing $^{375}$Val-$^{376}$Leu of human MAP kinase ERK1 [e.g. Ile-Phe-Gln-Glu-Thr-Ala-Arg-Phe-Gln-Pro-Gly-Val-Leu-Glu-Ala-Pro (SEQ ID NO:12)].

The monoclonal antibody to human MAP kinase ERK1 as generated in accordance with the present invention binds to human MAP kinase ERK1 with high sensitivity and, as such, is of great value as an assay reagent for human MAP kinase ERK1. Moreover, since this monoclonal antibody facilitates determination of human MAP kinase ERK1 in the vital organs and tissues, it can be a useful tool for acquiring basic information such as the distribution of the protein in vivo on human MAP kinase ERK1. While enzyme immunoassay (EIA), fluorescent antibody assay, and RIA are generally used for the detection of human MAP kinase ERK1 in the vital organs and tissues, EIA is particularly preferred. Moreover, for estimating the size of the human MAP kinase ERK1 present in an organ or tissue using the antibody of the invention, Western blotting for protein analysis is an effective procedure. This procedure typically comprises subjecting a crude extract of an organ or tissue or a partially purified preparation thereof to polyacrylamide gel electrophoresis, transferring the protein to a membrane filter, and carrying out the detection using the anti-human MAP kinase ERK1 antibody labeled with horseradish peroxidase (HRP).

It is possible, likewise, to construct an antibody affinity column using techniques well known to those skilled in the art for the purification of human MAP kinase ERK1, by taking advantage of the binding affinity of the antibody of the invention for human MAP kinase ERK1.

The antibody for use in the detection or assay of human MAP kinase ERK1 may be a fraction of its molecule, [e.g. $F(ab')_2$, Fab', or Fab]. Particularly the antibody to which a label is to be directly conjugated is preferably the Fab' fraction.

As mentioned above, the monoclonal antibody of the present invention can be used as a reagent in the immunochemical determination of human MAP kinase ERK1.

By such an immunochemical procedure for assaying human MAP kinase ERK1, the concentration and activity of human MAP kinase ERK1 in the vital tissues or cells can be determined. This technique is of great use in that the association of MAP kinase with various diseases can be advantageously explored by quantitating human MAP kinase ERK1 in various tissues and cells.

For an immunological assay using a set of two antibodies, a monoclonal antibody of the invention can be used in combination with another monoclonal antibody or a polyclonal antibody of the invention. For example, the combination of anti-human MAP kinase ERK1 monoclonal antibody and polyclonal antibody or the combination of anti-human MAP kinase ERK1 monoclonal antibody and anti-active-form MAP kinase monoclonal or polyclonal antibody can be mentioned. Moreover, for improvement in assay sensitivity, 3 or more different antibodies can be used in a suitable combination.

In addition to the anti-human MAP kinase ERK1 antibody described above, the inventors utilizing a peptide (synthetic peptide) created by phosphorylating the amino acid sequence corresponding to the phosphorylatable region of MAP kinase as the immunogen succeeded in constructing an antibody having a specific binding affinity for active-form MAP kinase. An example of said synthetic peptide is His-Thr-Gly-Phe-Leu-(Thr-$PO_3H_2$)-Glu-(Tyr-$PO_3H_2$)-Val-Ala-Thr-Arg (SEQ ID NO:1). The rationale for the use of such a synthetic peptide is that since the concurrent phosphorylation of the two phosphorylation sites in MAP kinase ($^{202}$Thr and $^{204}$Tyr in human ERK1 and $^{185}$Thr and $^{187}$Tyr in human ERK2) is considered necessary and sufficient for allowing the MAP kinase to function as a protein phosphorylase, the amino acid sequence around these sites was chosen.

For the production of a polyclonal antibody to active-form MAP kinase, a warm-blooded animal is inoculated with an immunogenic fragment peptide such as the synthetic peptide described above either as it is or as conjugated to said carrier protein beforehand. The warm-blooded animal that can be used for production of this polyclonal antibody includes a variety of warm-blooded mammalian animals (e.g. rabbit, sheep, bovine, rat, mouse, guinea pig, horse, swine, etc.) and avian species (e.g. chicken, pigeon, duck, goose, quail, etc.), among others. The inoculum size should be large enough but need not be too large for the production of the desired antibody. When the rabbit is to be immunized, for instance, sufficient antibody titers can be harvested in many cases when 1 mg/dose of the antigen emulsified in 1 ml of saline together with Freund's complete adjuvant is administered subcutaneously at the back and the hindpaw footpad 5 times at 4-week intervals. For harvesting the antibody so secreted from the warm-blooded animal, e.g. rabbit, blood is drawn from the auricular vein generally during the period of day 7 to day 12 after the last inoculation and centrifuged to separate serum. The desired polyclonal antibody can be generally purified by subjecting the antiserum separated as above to affinity chromatography using a stationary phase coupled to the corresponding antigenic peptide and recovering the adsorbed fraction.

For the production of the monoclonal antibody to active-form MAP kinase, the methods described for the production of the monoclonal antibody to human MAP kinase ERK1 can be employed.

The anti-phosphorylated peptide antibody (antibody to active-form MAP kinase) of the present invention binds to active-form MAP kinase with high sensitivity and as such is of great value as an assay reagent for active-form MAP kinase, that is to say as a reagent for determining MAP kinase activity. By using this antibody, MAP kinase activity can be detected or assayed without resort to any radioactive reagent. Moreover, the ease of assaying MAP kinase in the vital organs and tissues is of great value in generating basic biological information about MAP kinase. While enzyme immunoassay (EIA), fluorescent antibody assay, and RIA are generally used for the detection of active-form MAP kinase in the vital organs and tissues, EIA is particularly preferred. Moreover, for estimating the size of the active-form MAP kinase present in an organ or tissue using the antibody of the invention, Western blotting is an effective procedure. This procedure typically comprises subjecting a crude extract of an organ or tissue or a partially purified preparation thereof to polyacrylamide gel electrophoresis, transferring the proteins to a membrane filter, and carrying out the detection using the anti-active-form MAP kinase antibody labeled with HRP.

It is also possible to construct an antibody affinity column for the purification of active-form MAP kinase, by taking advantage of the binding affinity of the anti-active form MAP kinase antibody of the invention for active-form MAP kinase.

The antibody molecule for use in the detection or assay of active-form MAP kinase may be a fraction thereof (e.g. F(ab')$_2$, Fab', or Fab). Particularly the antibody molecule to which a label is to be directly conjugated is preferably the Fab' fraction.

As mentioned above, the anti-active-form MAP kinase antibody (anti-phosphorylated peptide antibody) of the present invention can be used as a reagent in the immunochemical determination of active-form MAP kinase.

By such an immunochemical procedure for assaying active-form MAP kinase, the concentration of active-form MAP kinase, that is to say MAP kinase activity, in the vital tissues or cells can be determined. This technique is of great use in that the association of MAP kinase activity with various diseases can be advantageously investigated.

Furthermore, by using the anti-human MAP kinase ERK1 antibody (preferably monoclonal antibody) of the invention in combination with the above anti-active-form MAP kinase antibody (anti-phosphorylated peptide antibody) of the invention, active-form human MAP kinase ERK1, for instance, can be assayed selectively, without the interference of human MAP kinase ERK2 and other species of MAP kinase that may be present, whether in active-form or in inactive-form, typically in a sandwich enzyme immunoassay system. Similarly, by using the antibody specific for a given species of MAP kinase in combination with the anti-active-form MAP kinase antibody, the corresponding species of active-form MAP kinase can be specifically assayed. For example, active-form ERK2 alone can be selectively assayed by using the antibody of the invention which is specific for MAP kinase ERK2 in combination with the anti-active-form MAP kinase antibody of the invention. In other words, ERK1 activity and ERK2 activity can be quantitated independently of each other.

The antibody specific for any one of said various species or forms of MAP kinase can be produced by immunizing a mammal with either human MAP kinase ERK1 or human MAP kinase ERK2, a mutein or a fragment peptide thereof in the first place. Then, for the production of a polyclonal antibody, the serum separated from the immunized animal is purified. When the desired antibody is a monoclonal antibody, spleen cells from the immunized animal are subjected to cell fusion with lymphoid cells from a mammal followed by cloning. In using said MAP kinase, mutein or fragment peptide for immunization, the MAP kinase may be coupled to a carrier protein in the first place and the resulting complex be used as the immunogen. The carrier protein that can be used includes but is not limited to bovine serum albumin, bovine thyroglobulin, and hemocyanin.

When a carrier-protein complex is used, the coupling ratio of carrier protein to MAP kinase (by weight) is about 0.1 through 30/1. The preferred ratio is about 0.5–5/1.

For the coupling reaction between hapten and carrier, a variety of condensing agents can be employed, although the use of glutaraldehyde or a carbodiimide reagent is particularly preferred.

Figure 6:
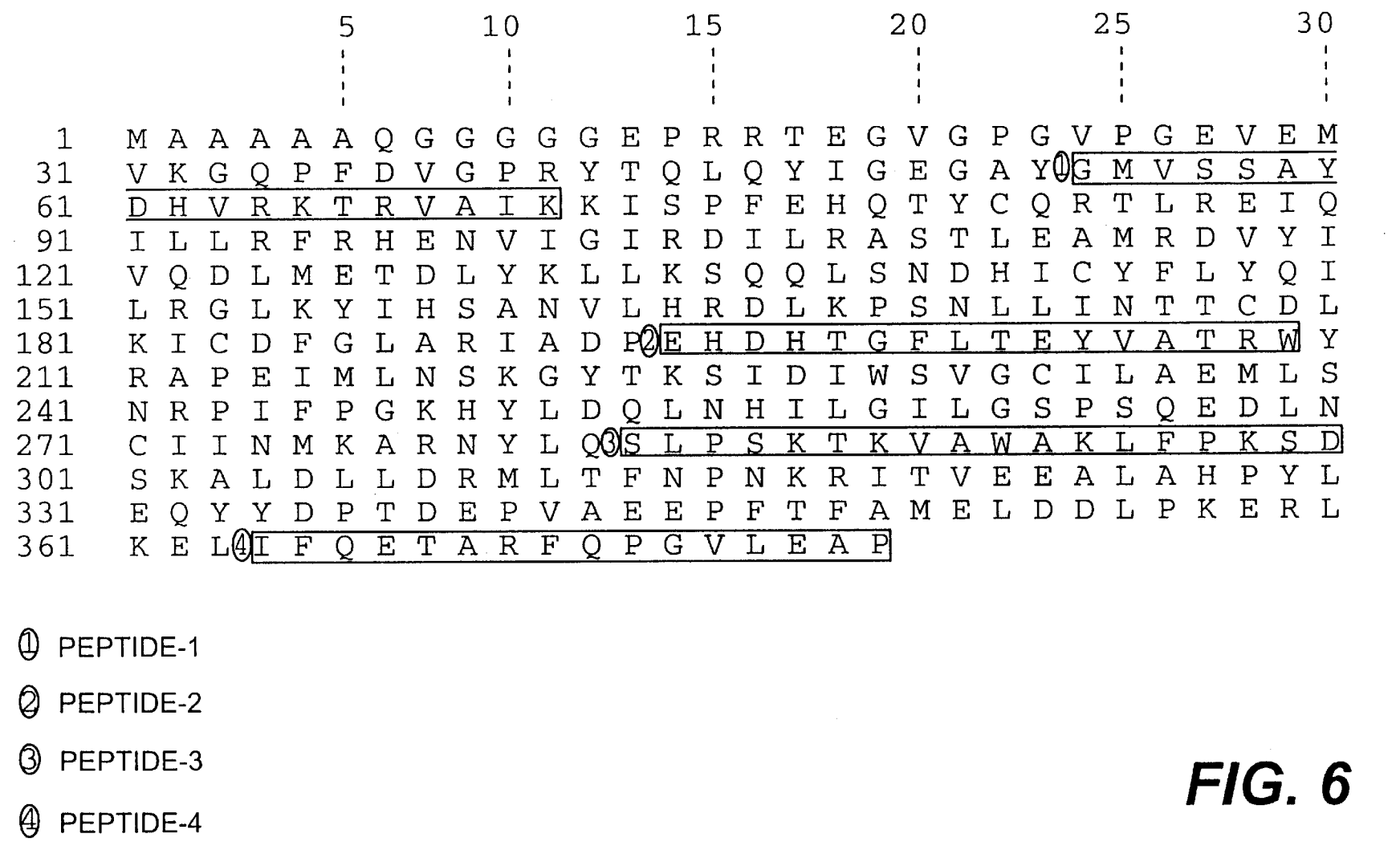

The fragment peptide of human MAP kinase ERK1 which can be used advantageously includes, referring to the SEQ ID NO:8 for human ERK1 in FIG. 6, peptide-1 which corresponds to the sequence from position 54 to position 71 (SEQ ID NO:9), peptide-2 corresponding to the sequence from position 194 to position 209 (SEQ ID NO:10), peptide-3 corresponding to the sequence from position 283 to position 300 (SEQ ID NO:11), and peptide-4 corresponding to the sequence from position 364 to position 379 (SEQ ID NO:12), to each of which cysteine may be added as a linker at the N-terminus (SEQ ID NOS:13, 6, 2 and 3).

The fragment peptide of human MAP kinase ERK2 which can be used advantageously includes, referring to the SEQ ID NO:14 for human ERK2 in FIG. 11, peptide-5 which corresponds to the sequence from position 266 to position 283 (SEQ ID NO:15) and peptide-6 corresponding to the sequence from position 347 to position 360 (SEQ ID NO:16), to each of which cysteine may be added as a linker at the N-terminus (SEQ ID NOS: 4 and 5).

In the immunization with MAP kinase or a complex thereof for the production of a polyclonal antibody, a warm-blooded animal is inoculated with an immunogenic fragment peptide such as the synthetic peptide described above either as it is or as coupled to said carrier protein beforehand. The warm-blooded animal that can be used for production of this polyclonal antibody includes a variety of warm-blooded mammalian animals (e.g. rabbit, sheep, bovine, rat, mouse, guinea pig, horse, swine, etc.) and avian species (e.g. chicken, pigeon, duck, goose, quail, etc.), among others. The inoculum size should be large enough but need not be too large for the production of the desired antibody. When the rabbit is to be immunized, a sufficient antibody titer can be obtained in many cases when 1 mg/dose of the antigen emulsified in 1 ml of saline together with Freund's complete adjuvant is administered subcutaneously at the back and the hindpaw footpad 5 times at 4-week intervals. For harvesting the antibody so produced from the warm-blooded animal, e.g. rabbit, blood is drawn from the auricular vein usually during the period of day 7 to day 12 after the last inoculation and centrifuged to separate serum. The desired polyclonal antibody can be generally purified by subjecting the antiserum separated as above to affinity chromatography using a stationary phase carrying the corresponding antigen peptide and recovering the adsorbed fraction.

The preferred host animal to be immunized for the production of a monoclonal antibody includes rats and mice. For immunizing a mouse, for instance, any of the intraperitoneal, intravenous, intramuscular, intradermal and subcutaneous routes can be employed but it is generally preferable to choose the subcutaneous, intraperitoneal or intravenous route. Most desirable is the subcutaneous route. The immunization interval, immunizing dose and other parameters are also widely variable and many alternatives are possible. A typical routine procedure comprises immunizing the animal twice to about six times at intervals of 2 weeks and excise the spleen about 1–5 days, preferably about 2–4 days, after the last immunization for harvesting splenocytes. The inoculum size is not less than about 0.1 $\mu$g peptide/mouse/dose and preferably about 10 $\mu$g–300 $\mu$g/mouse/dose. A recommended protocol suggests performing blood sampling prior to isolation of the spleen and confirming a sufficient elevation of the blood antibody titer before subjecting splenocytes to cell fusion.

The cell fusion mentioned above is typically carried out between the harvested mouse spleen cell and a lymphoid cell line such as a homologous or heterologous (preferably homologous) myeloma cell line carrying a suitable marker such as hypoxanthine-guanine phosphoribosyl transferase deficiency (HGPRT$^-$) or thymidine kinase deficiency (TK$^-$) [e.g. P3-X63-Ag·8U1, Ichimori et al., Journal of Immunological Methods, 80, 55, 1985]. Typically the method of Kohler and Milstein [Nature, 256, 495, 1975] is used for cell fusion. Thus, for example, myeloma cells and spleen cells in a ratio of about 1:5 are suspended in e.g. a 1:1 mixture of Iscove's medium and HAM F-12 medium (hereinafter referred to briefly as IH medium) and fused with the aid of a fusion promoter such as Sendai virus or polyethylene glycol (PEG). Of course, other fusion promoters such as dimethyl sulfoxide (DMSO) can be added as alternatives. Generally the average molecular weight of PEG used for this purpose is about 1000–9000, the reaction time is about 0.5–30 minutes, and the concentration is about 10–80%, for instance. To mention a preferred protocol, cell fusion can be efficiently accomplished using about 35–55% PEG 6000 in about 4–10 minutes. The fusion cell can be selectively expanded in a medium such as hypoxanthine-aminopterin-thymidine medium [HAT medium; Nature, 256, 495, 1975].

The culture supernatants of grown cells are screened for productivity of the desired antibody. This screening for antibody titer can be carried out in the following manner. As a first step, the production of an antibody reactive against the antigen peptide used for immunization is checked. While this examination can be made by radioimmunoassay (RIA) or enzyme immunoassay (EIA), each of these techniques is open to a variety of modifications. A typical EIA procedure is described below. The rabbit anti-mouse immunoglobulin antibody, for instance, is coupled to a solid phase such as cellulose beads beforehand in the conventional manner. This antibody-coupled solid phase is added to the culture supernatant to be analyzed or mouse serum and allowed to react at a constant temperature (about 4–40° C.; the same applies hereinafter) for a given time. The reaction product is then rinsed thoroughly and the enzyme-labeled antigenic peptide (an enzyme and the antigen peptide are coupled and purified in the routine manner) is added and allowed to react at a constant temperature for a given time. After the reaction product is rinsed thoroughly, a substrate for the enzyme is added and the reaction is carried out at a constant temperature for a given time. Then, the colored reaction product is quantitated on the basis of absorbance or the intensity of fluorescence.

The wells containing cells showing growth in a screening medium and antibody activity against the antigenic peptide used for immunization are selected and these cells are preferably cloned by the limiting dilution method or the like. The supernatant of the cloned cells is subjected to the same screening as above and the cells in wells showing high antibody titers are expanded whereby a monoclonal antibody-producing hybridoma clone reactive to the same antigenic peptide as used for immunization is obtained.

This cloned hybridoma is expanded in a liquid medium. Typically, the cloned hybridoma is cultured in a liquid medium, such as RPMI-1640 [Moore, G. E. et al., Journal of American Medical Association, 199, 549, 1967] supplemented with about 0.1–40% of bovine serum, for about 2–10 days, preferably about 3–5 days. In this manner, the desired monoclonal antibody can be harvested from the culture fluid. As an alternative, the antibody can be obtained by inoculating a mammal intraperitonally with the hybridoma, allowing the cells to grow in situ, and collecting the ascites. For this purpose, assuming that the mouse is used as said mammal, typically BALB/c mice pretreated with mineral oil or the like are inoculated intraperitoneally with about $1\times10^4$–$1\times10^7$ cells, preferably about $5\times10^5$–$2\times10^6$ cells, of the hybridoma and after about 7–20 days, preferably about 10–14 days, the ascites fluid is collected. The antibody secreted and accumulated in the ascites fluid is subjected to a purification procedure such as ammonium sulfate fractionation, DEAE-cellulose column chromatography or the like, whereby the objective monoclonal antibody can be easily isolated as a pure immunoglobulin.

The above procedure provides an anti-MAP kinase monoclonal antibody.

The anti-MAP ERK1 antibody of the present invention is binding to human and rat MAP kinase ERK1 but not biding to human and rat MAP kinase ERK2. On the other hand, the anti-MAP kinase ERK2 antibody of the invention is binding to human and rat MAP kinase ERK2 but not binding to human and rat MAP kinase ERK1. Therefore, these antibodies can be used as reagents for the detection, assay, purification and immunochemical studies of MAP kinase.

Moreover, the ease of assaying MAP kinase in the vital organs and tissues is of great value for generating basic information such as the distribution of the protein in vivo about MAP kinase. While enzyme immunoassay (EIA), fluorescent antibody assay, and RIA are generally used for the detection of MAP kinase in the vital organs and tissues, EIA is particularly preferred. Moreover, for estimating the size of the MAP kinase present in an organ or tissue using the antibody of the invention, Western blotting for protein analysis is an effective procedure. This procedure typically comprises subjecting a crude extract of an organ or tissue or a partially purified preparation thereof to polyacrylamide gel electrophoresis, transferring the proteins to a membrane filter, and carrying out the detection using the anti-MAP kinase antibody labeled with HRP.

In addition, it is possible to construct an antibody affinity column using techniques well known to those skilled in the art for the purification of MAP kinase (ERK1 or ERK2), by taking advantage of the binding affinity of the antibody of the invention for MAP kinase.

The antibody molecule for use in the detection or assay of MAP kinase may be a fraction thereof (e.g. F(ab')$_2$, Fab', or Fab). Particularly the antibody molecule to which a label is directly conjugated is preferably the Fab' fraction.

As mentioned above, the antibody of the invention can be used as a reagent in the immunochemical determination of MAP kinase.

By such an immunochemical procedure for assaying MAP kinase, the concentration and activity of MAP kinase in vital tissues or cells can be determined. This technique is of great use in that the association of MAP kinase with various diseases can be advantageously investigated by measuring an amount or activity of MAP kinase in various tissues and cells.

The present assay method facilitates the diagnosis of various MAP kinase-related diseases and the identification of their pathologic causes. For example, the MAP kinase content and/or activity in diseased tissue or cells may be compared with that in normal tissue or cells, so as to obtain an established diagnosis, classify the disease, choose the appropriate therapy or drug, identify the pathologic cause, or for other purposes. Such diseases may be any one caused by change of MAP kinase contents and/or activities in various tissues or cells, and, among others, they include cancer-associated diseases (e.g., brain tumor, gastric cancer, lung cancer, thyroid cancer, pancreatic cancer, leukemia), metabolic disorders (e.g., diabetes mellitus), circulatory disease (e.g., arteriosclerosis), allergic diseases (e.g., asthma, pollenosis, atopic dermatitis), central nervous system diseases (e.g., Alzheimer's disease, Parkinsonism, senile dementia) and bone/joint diseases (e.g., rheumatism).

Also, the use of the present assay method enables the elucidation of the mechanisms of action of various drugs. More specifically, the action point of a particular drug can be determined by comparing the MAP kinase contents and/or activities in various tissues or cells in the presence of the drug with those in the absence of the drug.

For an immunological assay using a set of two antibodies, the antibodies of the present invention can be used in combination. Moreover, for improvement in assay sensitivity, 3 or more different antibodies can be used in a suitable combination.

The antibody immobilized on a solid phase (immobilized antibody), which is used in the assay of a MAP kinase such as human MAP kinase ERK1 and its activated form, includes a broad variety of supports such as gel beads [e.g. agarose gel beads (Sepharose 4B, Sepharose 6B (tradename, Pharmacia Fine Chemicals, Sweden))], dextran gels [e.g. Sephadex G-75, Sephadex G-100 and Sephadex G-200 (the trademark of Pharmacia Fine Chemicals, Sweden)], polyacrylamide gels [e.g. Bio-Gel P-30, Bio-Gel P-60 and Bio-Gel P-100 (the trademark of Biorad Laboratories, USA)], cellulose granules [e.g. Avicel (the trademark of Asahi Chemical Industry Co., Ltd.)], ion-exchange cellulose [e.g. diethylaminoethylcellulose, carboxymethylcellulose, etc.], and physical adsorbents [such as glass (e.g. glass beads, glass rods, aminoalkyl glass beads, aminoalkyl glass rods, etc.)], silicone flakes, styrenic resin [e.g. polystyrene beads, polystyrene granules], immunoassay plates [e.g. the immunoplate manufactured by Nunc, Denmark], ion-exchange resins {e.g weakly acidic cation exchange resins [e.g. Amberlite IRC-5 (the trademark of Rohm & Haas Co., USA), Zeo-karb 226 (tradename, Permutit, West Germany)], and weakly basic anion exchange resins [e.g. Amberlite IR-4B and Dowex 3 (the trademark of Dow Chemical Co., USA)]}, among others well known to those skilled in the art.

The antibody can be immobilized to the solid phase by well-known procedures. Typical are the bromocyan method and glutaraldehyde method which are described in TAISHA (Metabolism), 8, 696, 1971. As a more expedient alternative, the antibody can be physically adsorbed on the solid phase surface.

The label which can be used for labeling the antibody includes radioisotopes, enzymes, fluorescent substances, and chemiluminescent substances but the use of enzymes is preferred. Particularly preferred is an enzyme that is stable and has high specific activity, such as peroxidase, alkaline phosphatase, β-D-galactosidase, glucose oxidase, etc. The most preferred is peroxidase. The source of peroxidase is not critical and includes horseradish, pineapple, fig, sweet potato, kidney bean, corn, etc. Particularly preferred is horseradish peroxidase which is extracted from horseradish.

The coupling of peroxidase to antibody can be conveniently carried out by using a maleimidated peroxidase, utilizing the thiol group of the antibody molecule Fab'.

The introduction of a maleimide group into peroxidase can be achieved via the amino group of peroxidase. For this purpose, an N-succinimidylmaleimide carboxylate derivative can be employed. Particularly, N-(γ-maleimidobutyloxy)succimide (hereinafter referred to sometimes as GMBS) can be used with advantage. This implies that there is no problem if a certain group is interposed between the maleimide group and the peroxidase molecule. To react GMBS with peroxidase, the two reactants are caused to interact in a buffer solution of pH about 6–8 at a temperature of about 10–50° C. for about 10 minutes to about 24 hours. The buffer solution may for example be 0.1M phosphate buffer pH 7.0. The resulting maleimidated peroxidase can be purified typically by gel chromatography. The media for gel chromatography can be selected from among Sephadex G-25 (the trademark of Pharmacia Fine Chemicals, Sweden), Bio-Gel P-2 (the trademark of Biorad Laboratories, USA), and so on.

The reaction between the maleimidated peroxidase and the antibody molecule can be carried out by permitting the two reactants to interact in a buffer solution at a temperature of about 0°–40° C. for about 1–48 hours. The buffer that can be used for this purpose may for example be a 0.1M phosphate buffer solution (pH 6.0) containing 5 mM sodium ethylenediaminetetracetate. The peroxidase-labeled antibody thus obtained can be purified typically by gel chromatography. The media that can be used for this gel chromatography includes Sephadex G-25 [Pharmacia Fine Chemical, Sweden] and Bio-Gel P-2 [Biorad Laboratories, USA], among others.

As an alternative, a thiol group may be introduced into peroxidase and the latter be then reacted with the maleimidated antibody molecule.

For direct conjugation of an enzyme other than peroxidase to the antibody, the procedure described above for peroxidase can be basically followed. The glutaraldehyde method, periodic acid method, and water-soluble carbodiimide method can also be employed.

The sample to be analyzed in the assay systems according to the invention includes extracts of various tissues, cells, cell lines, or microorganisms as well as the corresponding culture supernatants. A typical assay procedure employing the peroxidase label, for instance, is described below. It should be noted that the label is not restricted to peroxidase.

(1) Add a sample containing MAP kinase such as human MAP kinase ERK1 or active-form MAP kinase to the antibody immobilized to a solid phase to contact the sample with the antibody and to carry out an antigen-antibody reaction. Then, add the above peroxidase-anti-MAP kinase antibody complex (enzyme-labeled antibody) to generate a reaction product.

(2) To the reaction product obtained in Step (1), added a substrate for peroxidase and measure the absorbance or intensity of fluorescence of the resulting product to estimate the enzymatic activity of the reaction product.

(3) Follow Steps (1) and (2) on standard solutions containing known quantities of MAP kinase such as human MAP kinase ERK1 or active-form MAP kinase for constructing a standard curve correlating the absorbance or intensity of fluorescence with the quantity of the standard protein.

(4) Compare the absorbance or intensity of fluorescence measured for the sample being analyzed that contains an unknown quantity of MAP kinase to the standard curve to find the MAP kinase content of the sample.

Using the antibodies of the invention, various species of MAP kinase such as human MAP kinase ERK1, active-form MAP kinase, etc. can be purified. Such purification can be carried out by affinity column chromatography using the antibody of the invention.

The affinity column chromatography mentioned above can be carried out by preparing a column packed with an antibody-maxtrix conjugate, loading a solution containing MAP kinase such as human MAP kinase ERK1 or active-form MAP kinase on the column to let the kinase adsorbed, and eluting the kinase from the column.

The matrix that can be used include the various substances mentioned hereinbefore. Gel beads as well as various synthetic resin matrices can be used with particular advantage. For example, CNBr-activated Sepharose 4B (Pharmacia Fine Chemicals), Affi-Gel 10 and Affi-Gel 15 (both tradenames, Biorad Laboratories), etc. can be employed.

The antibody can be conjugated to the matrix by the well-known procedures. For example, the bromocyan method and glutaraldehyde method which are described in TAISHA (Metabolism), 8, 696, 1971 can be mentioned. The method employing 1-ethyl-3-(3-dimethylaminopropyl)-carbodiimide, the activated ester method, etc. can also be employed. However, as a more expedient procedure, the antibody can be physically adsorbed on the matrix surface.

For a purification procedure using the antibody-matrix complex thus obtained, a solution of MAP kinase in an appropriate buffer is applied to an antibody column packed with the antibody-matrix complex to allow the MAP kinase to be adsorbed. After the column is washed with the same buffer solution, the specifically adsorbed MAP kinase is eluted. This elution of the specifically adsorbed MAP kinase can be carried out typically using a buffer of either low pH or high pH or a high-salt buffer.

The above-mentioned buffer of low pH includes but is not limited to 0.17M glycine-HCl buffer pH 2.3 and 0.1M dibasic sodium citrate-HCl buffer pH 1.8.

The high-pH buffer includes but is not limited to aqueous ammonia pH 11 and 0.2M sodium borate buffer pH 11.7.

The high-salt buffer includes but is not limited to 6M guanidine hydrochloride solution and 7M urea solution.

The above-mentioned elution can be carried out batch-wise or column-wise.

The eluted antigen is purified typically by dialysis. For example, when elution was carried out with a low-pH buffer, the eluate is first neutralized with a high-pH buffer such as O.lM sodium carbonate buffer (pH 10.5) and when elution was carried out with a high-pH buffer, the eluate is neutralized with a low-pH buffer such as 0.1M glycine-HCl buffer (pH 3.0). The neutralized eluate is then dialyzed typically against 0.02M phosphoric acid-NaCl buffer containing 0.1% $NaN_3$ (pH 8.0). The antigen solution eluted with a high-salt buffer can be directly dialyzed against said phosphoric acid-NaCl buffer and the dialyzate stored. It is also possible to freeze-dry the above-mentioned eluates or dialyzates and store the lyophilizates. The MAP kinase purified by using the antibodies of the present invention is extremely high in purity and potency. Therefore, these antibodies are very useful instruments for exploration into various intracellular signal transduction systems.

In this specification and the accompanying drawings, where bases, amino acids, etc. are represented by abbreviations, the abbreviations recommended by IUPAC-IUB Commission on Biochemical Nomenclature or those used conventionally in the art are employed. The following is a partial list of such abbreviations. It should be understood that in case any amino acid may exist as optical isomers, the L-compound is meant unless otherwise indicated.

DNA: deoxyribonucleic acid
CDNA: complementary deoxyribonucleic acid
A: adenine
T: thymine
G: guanine
C: cytosine
RNA: ribonucleic acid
dATP: deoxyadenosine triphosphate
dTTP: deoxythymidine triphosphate
dGTP: deoxyguanosine triphosphate
dCTP: deoxycitidine triphosphate
ATP: adenosine triphosphate
Tdr: thymidine
EDTA: ethylenediaminetetracetic acid
SDS: sodium dodecyl sulfate
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gin: glutamine
Clz: 2-chlorobenzyloxycarbonyl BrZ: 2-bromobenzyloxycarbonyl
Bzl: benzyl
Boc: t-butoxycarbonyl

EXAMPLES

The following examples are intended to describe the present invention in further detail and should by no means be construed as defining or limiting the scope of the invention.

The hybridoma as a producer of antibodies according to the present invention has been deposited for accession as follows.

| Animal cell | (IFO) IFO No. | (NIBH) FERM No. |
|---|---|---|
| Mouse hybridoma HE113 | 50453 (1995-3-28) | BP-5456 (1995-4-4) |

IFO: Institute for Fermentation (Osaka)
NIBH: National Institute for Bioscience and Human Technology The numerals in parentheses denote the date of deposit.

The hybridoma was deposited on Apr. 4, 1995 at National Institute for Bioscience and Human Technology under the accession number of FERM P-14876. The deposit has been converted to a deposit under the Budapest Treaty, and is stored at National Institute for Bioscience and Human Technology under the accession number of FERM BP-5456.

Example 1
Preparation of Human MAP Kinase ERK1 Protein

The sequence of the cDNA coding for the human MAP kinase ERK1 protein is known [David L. Charest et al., Mol. Cell. Biol., 13, 4679–4690, 1993]. To prepare this cDNA, the two different DNA strands shown in FIG. 1 were synthesized [SEQ ID NO:17 and SEQ ID NO:18). Using the total RNA obtained from the cultured human cell line WI-38 [Exp. Cell. Res., 25, 585, ATCC CCL-75) as a template, a cDNA was synthesized by using a random hexanucleotide primer and a reverse transcriptase (GIBCO BRL, Super Script). To this cDNA Taq DNA polymerase (Cetus) was added as well as the above 2 different synthetic primer DNAs, and a polymerase chain reaction using a cycle of 94° C.×1 min., 55° C.×1 min. and 72° C.×3 min. was carried out for a total of 35 cycles. The reaction product was then subjected to 5% acrylamide gel electrophoresis and the DNA chain segment showing the mobility predicted from the chain length of human ERK1 cDNA was cut out and suspended in 10 mM Tris-HCl buffer containing 1 mM EDTA. The suspension was allowed to stand overnight to elute the cDNA from the gel slice. Using this eluate, an expression system for the protein in E. coli was constructed by the method illustrated in FIG. 2. For inductive expression, the bacteriophage T7 promoter system was used [Studier, F. W. et al., Methods in Enzymology, 185, 60–89].

Figure 3:
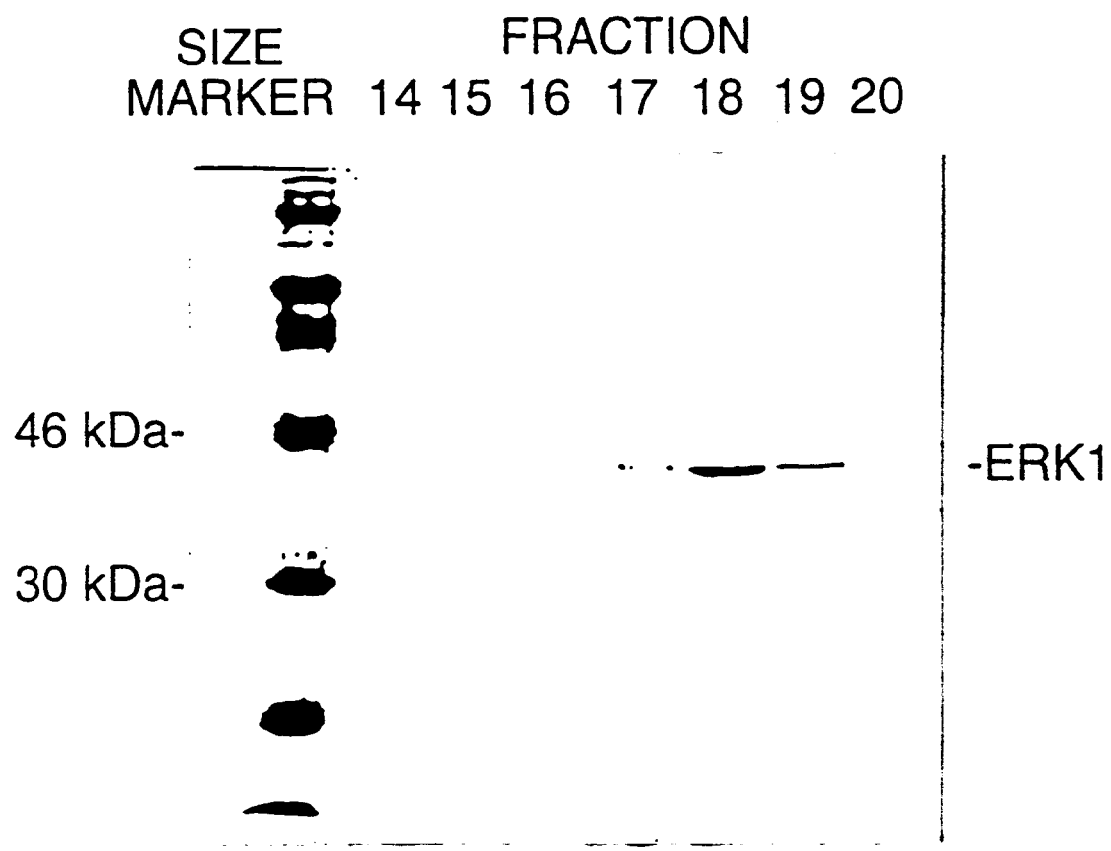
FIG. 3 shows the fractionation by Mono Q column (Pharmacia) chromatography, after SDS-PAGE and Coomassie staining, at the final stage of purification of human MAP kinase ERK1 expressed in *E. coli*.

The nucleotide sequence of the cloned cDNA was confirmed by the synthetic chain-termination method using dideoxynucleotides [Sanger, F. et al. Proc. Natl. Acad. Sci. U.S.A., 74, 5463–5467, 1977]. The procedure of Boulton, T. G. et al. [Cell, 65, 663–675] was followed for the expression and purification of the protein. Thus the protein purified to the extent of giving a substantially single band in Coomassie Brilliant Blue (R-250) staining after SDS-polyacrylamide gel electrophoresis [Laemmli et al., Nature, 227, 680–685, 1970] (FIG. 3) was obtained.

Example 2
Acquisition of Anti-human MAP Kinase ERK1 Monoclonal Antibody (1) Immunization A BALB/c mouse (♀, 8 weeks old) was subcutaneously inoculated with a mixture of 10 µg of the human MAP kinase ERK1 obtained in Example 1 and Freund's complete adjuvant (Difco Laboratories, USA). After 2 weeks, the same mouse was subcutaneously inoculated with a mixture of 10 µg human MAP kinase ERK1 obtained in Example 1 and Freund's incomplete adjuvant (Difco). The same immunizing procedure was further carried out 5 times at intervals of about 2 weeks. Seventeen (17) days after the last immunization, a solution of 100 µg human MAP kinase ERK1 in 50 mM Tris-HCl (pH 7.4) was intravenously administered to the same mouse.

(2) Cell fusion

From the mouse immunized in Step (1), the spleen was isolated 3 days after the last antigen immunization, and spleen cells for use in cell fusion were collected and suspended in MEM.

Mouse myeloma cell line P3-X63-Ag-8U1 (P3U1) was subcultured in GIT medium (Nippon Seiyaku) supplemented with 5% fetal calf serum under 5% $CO_2$-95% air. The cell fusion was carried out in accordance with the protocol established by Kohler and Milstein [Nature, 256, 495, 1975]. Thus, $6.9 \times 10^7$ P3U1 cells and $3.2 \times 10^8$ spleen cells from the mouse immunized as above were mixed and centrifuged. Then, 45% PEG 6000/0.5 ml MEM prewarmed to 37° C. was slowly added dropwise to the pellet. After 7 minutes, MEM warmed to 37° C. was added in 0.5 ml aliquots every 1 minute to make 15 ml, followed by centrifuging at 600×g (at room temperature) for 15 minutes, and the supernatant was discarded. The pellet was suspended in 210 ml of GIT medium supplemented with 5% fetal calf serum and seeded in a 96-well microtiter plate (Nunc, Naperville, Ill.), 100 µl per well. One day later, 150 µl/well of GIT medium (supplemented with 5% fetal calf serum) containing HAT (hypoxanthine $1 \times 10^{-4}$M, aminopterin $4 \times 10^{-7}$M, thymidine $1.6 \times 10^{-5}$M) (hereinafter referred to briefly as HAT medium) was added. Thereafter, ½ volume of the medium was changed to fresh HAT medium at 3-day intervals. The cells thus grown are hybrid cells.

(3) Screening of antibody-secreting cells

The human MAP kinase ERK1 purified by the procedure described in Example 1 was diluted with 10 mM carbonate buffer (pH 8.0) to 0.5 µg/ml, and the dilution was distributed to a 96-well immunoplate (Nunc), 100 µl per well. The plate was allowed to sit at 4° C. overnight, whereby the human MAP kinase ERK1 was coated to the solid phase. The immunoplate was rinsed with PBS, and to block the surplus binding sites, 250 µl of PBS containing 20% of Block Ace (Snow Brand Milk Products Co.) was added to each well and the plate was stored cold until needed. To the 96-well immunoplate coated with the human MAP kinase ERK1 by the above procedure, 100 µl/well of the hybridoma supernatant was added and the plate was incubated at room temperature for 2 hours. The culture supernatant was then discarded, and after rinse, HRP-labeled goat anti-mouse IgG antibody (Cappel, USA) was added as the secondary antigen. The plate was incubated at room temperature for an additional 2 hours. After removal of the secondary antibody, the wells were rinsed well and 100 µl of HRP substrate solution (sodium citrate buffer pH 5.5 containing 0.02% $H_2O_2$ and 0.15% o-phenylenediamine) was added and the reaction was allowed to proceed at 25° C. for 10 minutes. The enzymatic reaction was then stopped by adding 100 µl of 2N-sulfuric acid and using an automatic microplate colorimeter (MTP-32, Corona), the absorbance at 492 nm was measured. As a result, the presence of an antibody binding to human MAP kinase ERK1 was detected in one well.

(4) Cloning of the hybrid cells

The cells in the antibody-positive well were seeded at a density of 0.5 cell per well in a 96-well microtiter plate pre-seeded with $5\times10^4$ mouse thymocytes/well as nutrient cells to conduct cloning. As a result, one representative clone (mouse hybridoma HE113) was obtained.

(5) Production of the antibody

Using the hybridoma clone obtained in Step (4), BALB/c mice which had been intraperitoneally treated with 0.5 ml of mineral oil were inoculated in a dose of $1\times10^8$ cells/animal for ascites development. The ascites fluid was collected 10 days after intraperitoneal administration of the hybrid cells. From about 10 ml of each ascites fluid, the monoclonal antibody was purified by the method of Stehlin et al. [Journal of Biological Chemistry, 256, 9750–9754, 1981]. To remove fibrinoid matter from the ascite fluid, the fluid was centrifuged at 10,000×g for 15 minutes and, then, diluted with PBS (8.1 mM disodium phosphate, 1.5 mM potassium phosphate, 27 mM KCl, 137 mM NaCl, pH 7.2) to a concentration showing a 280 nm UV absorbance ($A_{280}$) of 12–14. To the diluted sample was added saturated ammonium sulfate solution to 47% concentration and the stirring was carried out at 4° C. for 60 minutes, followed by centrifugation (10,000 rpm, 15 min.) to give a pellet. The pellet was dissolved in 50 mM NaCl-20 mM Tris buffer (pH 7.9) and dialyzed against 2 l of the same buffer. After 2 hours, the dialysis fluid was replaced with 2 l of fresh buffer and the dialysis was further conducted for 15 minutes. The dialyzate thus obtained was centrifuged at 10,000 rpm for 15 minutes to remove sediments and the supernatant was adjusted to a concentration giving an $A_{280}$ absorbance value of 20–30. This sample was loaded on a 20 ml DEAE-cellulose column (Whatman $DE_{52}$) equilibrated using a sufficient quantity of 50 mM NaCl-Tris buffer. After the column was washed well with 50 mM NaCl-containing Tris buffer, fractionation was carried out on a 50 mM-500 mM NaCl gradient of the same buffer at a flow rate of 1.5 ml/min. The effluent was concentrated to provide a purified sample of monoclonal antibody HE113.

The SDS-polyacrylamide gel electrophoresis (SDS-PAGE) technique was used to check the purity of the antibody. Thus, after ammonium sulfate fractionation, the fraction that passed through a DEAE-cellulose column was reduced with 2-mercaptoethanol and using an acrylamide gel of 10% concentration, electrophoresis was carried out at a potential of 180 V for 2.5 hours. As a result, a couple of bands at ca 52 KDa for the H-chain and ca 28 KDa for the L-chain were detected.

Example 3

Characteristics of the Antibody (1) Western blot assay

Figure 4:
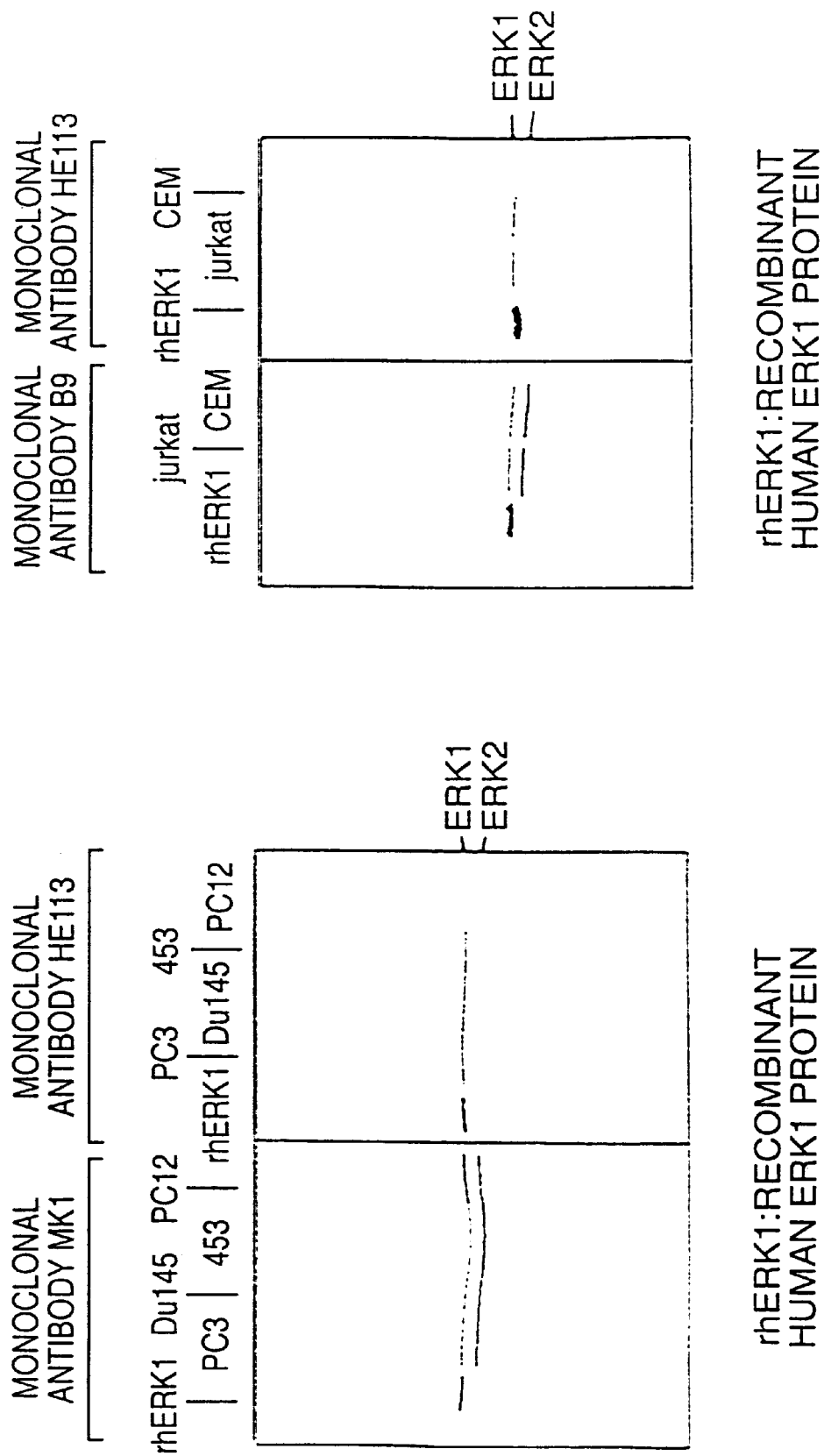
FIG. 4 shows a comparison of Western blots for various cells as obtained by using the anti-human MAP kinase ERK1 monoclonal antibody HE113 according to Example 3 and commercial anti-MAP kinase antibodies.

The human cell lines PC-3 (ATCC CRL-1435), DU145 (ATCC HTB-81), MDA-MB-453 (ATCC HTB-131), Jurkat (ATCC TIB-152) and CCRF-CEM (ATCC CCL-119) and the rat-derived cell line PC-12 (ATCC CRL-1721) were respectively cultured in the culture medium indicated in the corresponding ATCC catalog, using tissue culture dishes (Falcon 3003), until growth covered the entire surface. Each culture was lysed in a solution of SDS and 2-mercaptoethanol and heated at 95° C. for 5 minutes. This solution was subjected to SDS-PAGE using 10% gel and the protein was transferred onto a membrane filter and caused to react with the monoclonal antibody prepared in Example 2. Then, alkaline phosphatase-labeled goat anti-mouse IgG antibody was added so as to let a color be developed utilizing the phosphatase activity (FIG. 4). As a result, with all the human cell lines ERK1 was detected, but ERK2 was not detected. With the rat-derived cell line, neither ERK1 nor ERK2 was detected. With the commercial monoclonal antibodies (Clone MK1, Bio Design and Clone B9, BUI Catalog, 1993, p.33) used as controls, not only human ERK1 but also human ERK2, rat ERK1 and rat ERK2 were definitely detected, suggesting that the monoclonal antibody HE113 of the present invention specifically binds to human ERK1 only.

(2) EIA

Figure 5:
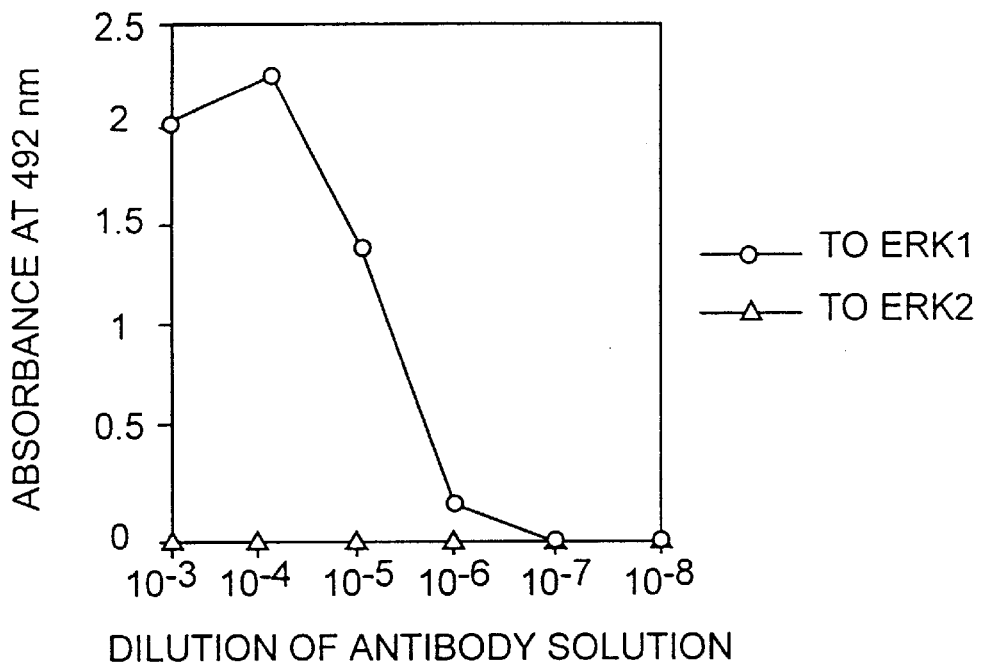
FIG. 5 shows the binding of the GST-human ERK1 fusion protein and GST-human ERK2 fusion protein of Example 3 by anti-human MAP kinase ERK1 monoclonal antibody HE113 in the EIA system.

Human ERK2 cDNA was cloned in the same manner as described in Example 1. In addition, human ERK1 cDNA and human ERK2 cDNA were respectively cloned into the plasmid pGEX-4T-2 (Pharmacia) and the human ERK1 and human ERK2 proteins were expressed as fusion proteins with GST (glutathione S-transferase) and purified with a glutathione-Sepharose (Pharmacia) column in accordance with the method of Smith, D. B. et al. [Gene, 67, 31–40]. Using immunoplates (Nunc) coated with these proteins, the binding capacity of the monoclonal antibody was investigated by the same EIA method as described in Example 2-(3). As a result, when the plate was coated with GST-human ERK1 protein, the monoclonal antibody showed strong binding, whereas no binding occurred when the plate was coated with GST-human ERK2 protein (FIG. 5). This result also indicates the high specificity for human ERK1 protein.

(3) Recognition sites of the antibody

Figure 7:
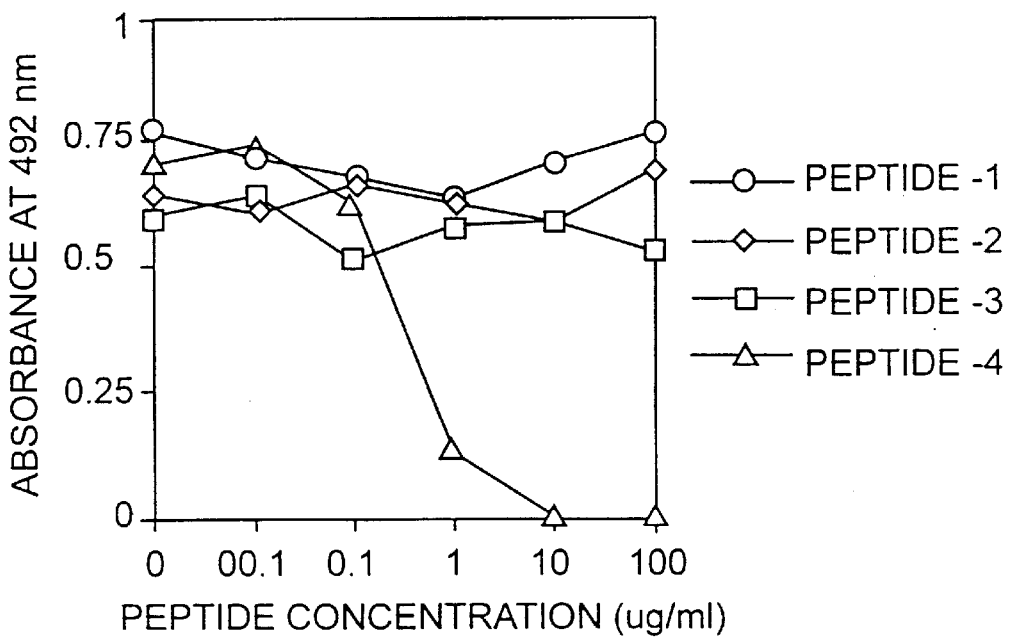
FIG. 7 shows the EIA analysis (Example 3) of the inhibition of the binding between the human ERK1 protein and anti-human MAP kinase ERK1 monoclonal antibody HE113 by the synthetic peptides shown in FIG. 6.

To ascertain the epitope of human ERK1 protein which is recognized by the monoclonal antibody obtained, synthetic peptides (peptide-1 through peptide-4; FIG. 6) (SEQ ID NO:9, SEQ ID NO:10, SEQ ID NO:11, SEQ ID NO:12) having the amino acid sequences of different regions of human ERK1 (SEQ ID NO:8) were respectively added to the above EIA system to investigate the influence of addition. The results (FIG. 7) showed that the antibody recognized the C-terminal sequence (peptide-4; SEQ ID NO:12) of the protein. Moreover, since this antibody is not binding to rat ERK1, it is reasonably inferable that the antibody recognizes a region containing $^{375}$Val-$^{376}$Leu, a point of difference between man and rat, as well.

Example 4

Determination of the Antibody Subclass

The subclass of the monoclonal antibody HE113 obtained in Example 2 was examined by the following procedure. The monoclonal antibody was coated onto a 96-well immunoplate, and after rinse, the antibodies (Cappel) to the rabbit anti-mouse $\gamma_1$, $\gamma_{2a}$, $\gamma_{2b}$, $\gamma_3$, κ, and λ chains, 100 μl each, were added. The immunoplate was then incubated at room temperature for 2 hours. After removal of the antibodies and rinse, HRP-labeled goat anti-rabbit IgG antibody (Cappel) was added and the plate was incubated at room temperature for 2 hours. After removal of the labeled antibody and thorough rinse, the enzymatic reaction was carried out by the procedure described in Example 2-(3) and the absorbance was measured. This analysis revealed that HE113 is an antibody belonging to the $\gamma_{2a}$, κ subclass.

Example 5

A Protocol for Assay of Human MAP Kinase Using the Antibody

Using the monoclonal antibody obtained in Example 2 in combination with a polyclonal antibody obtained by immunizing rabbits with a synthetic peptide having the amino acid sequence corresponding to the C-terminal region of human MAP kinase, a sandwich EIA protocol for detecting or assaying human MAP kinase ERK1 was developed.

(1) Preparation of a polyclonal antibody

A peptide comprising cysteine linked to the N-terminus of peptide-4 (FIG. 6) was synthesized and using GMBS [N-(maleimidobutyryloxy)succinimide; Dojin Kagaku Kenkyusho], the peptide was conjugated to bovine thyroglobulin (BTG, Sigma) via the SH group of cysteine. Rabbits (New Zealand White, male, 2.5 kg) were inoculated subcutaneously with a mixture of the above peptide-BTG conjugate (containing 0.2 mg of peptide) and Freund's complete adjuvant (Difco Laboratories, USA). Thereafter, the rabbits were inoculated with a similar mixture with Freund's incomplete adjuvant at 2-week intervals. The blood was drawn 1 week after the 4th inoculation and the serum was separated.

The serum was mixed with an equal volume of saturated ammonium sulfate solution and the precipitated protein was centrifugally recovered. The pellet thus obtained was dissolved in PBS (8.1 mM disodium phosphate, 1.5 mM potassium phosphate, 27 mM potassium chloride, 137 mM sodium chloride, pH 7.2) to make the same volume as the initial serum. This solution was filtered through a 0.22 μm filter (Millipore) and the filtrate was diluted 2-fold with 20 mM phosphate buffer (pH 7.0) and loaded on a HiTrap Protein G column (Pharmacia Biotech). After the column was washed with 10 ml of 20 mM phosphate buffer (pH 7.0), IgG was eluted with 3 ml of 0.1M glycine-HCl buffer (pH 2.7) and the eluate was neutralized with 150 μl of 1.0M Tris-HCl buffer (pH 9.0).

The resulting IgG fraction was diluted two-fold with 500 mM sodium chloride-20 mM phosphate buffer solution (pH 7.0) and loaded on a HiTrap NHS-activated column (Pharmacia Biotech) conjugated to the peptide used as the immunogen. Elution was carried out using 500 mM NaCl-100 mM glycine-HCl buffer solution (pH 2.0) and the eluate was neutralized in the same manner as above.

(2) Biotinylation of the antibody

The purified antibody was dialyzed against 0.1M NaHCO$_3$ buffer (pH 8.2) to a final concentration of 1 mg/ml. Then, 60 μg/ml of NHS-LC-Biotin (Pierce) was added and the mixture was continuously agitated at room temperature for 4 hours. The mixture was then dialyzed against PBS containing 0.01% of thimerosal at 4° C.

(3) Establishment of an EIA system

The monoclonal antibody obtained in Example 2 was diluted with 10 mM NaHCO$_3$ buffer (pH 8.0) to a concentration of 20 μg/ml and this dilution was added to a 96-well EIA plate (Corning, No. 430480), 100 μl per well, and allowed to stand at 4° C. overnight to let the antibody coupled to the solid phase. After the wells were rinsed twice with PBS (8.1 mM disodium phosphate, 1.5 mM potassium phosphate, 27 mM potassium chloride, 137 mM sodium chloride, pH 7.2), 300 μl of PBS containing 25% Block Ace (Snow Brand Milk Products Co.) was added to each well. The plate was stored cold until needed. In using the plate, it was first rinsed twice with PBS containing 0.05% of Tween 20. Then, a concentration series of GST-ERK1 fusion protein in said Block Ace-containing PBS was added, 100 μl per well. The plate was then allowed to sit at 4° C. overnight.

Figure 8:
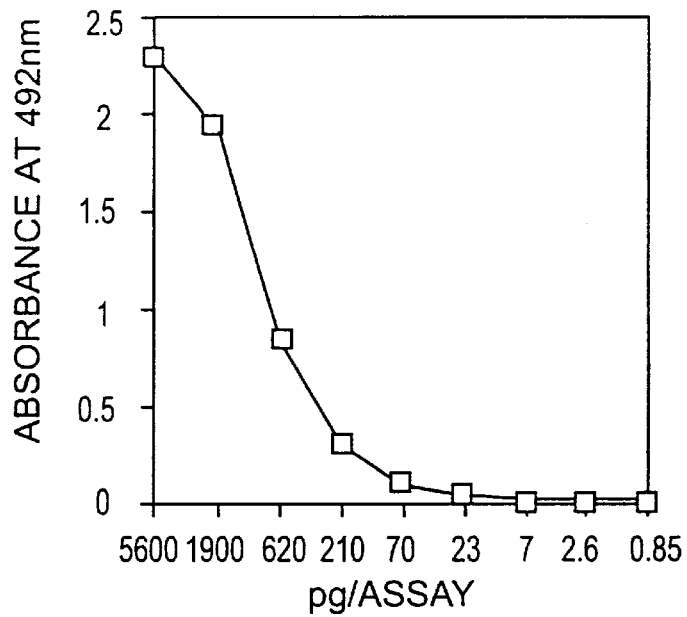
FIG. 8 shows the detection of GST-human MAP kinase ERK1 fusion protein by the sandwich EIA using anti-human MAP kinase ERK1 monoclonal antibody HE113 and anti-peptide-4 polyclonal antibody as described in Example 5.

After 3 rinses with PBS containing 0.05% of Tween 20, 1000-fold dilution of biotinylated polyclonal antibody was made with PBS containing 0.1% of BSA. The biotinylated polyclonal antibody was then added, 100 μl/well, and the plate was allowed to sit at room temperature for 2 hours. After 4 rinses with PBS containing 0.05% of Tween 20, a mixture of biotinylated horseradish peroxidase (HRP) and avidin (both from Vector Laboratories Vectastain Elite ABC Kit, diluted 1000-fold), previously admixed for 30 minutes, was added, 100 μl per well, and the plate was allowed to sit at room temperature for 1 hour. After 6 rinses with PBS containing 0.05% of Tween 20, HRP substrate solution was added for enzymatic reaction in the same manner as Example 2-(3) and the absorbance was measured at 492 nm. As a result, the detection limit for ERK1 in this assay system was found to be about 70 pg/assay (FIG. 8).

Reference Example 1

Synthesis of the Synthetic Peptide

His-Thr-Gly-Phe-Leu-(Thr-PO$_3$H$_2$)-Glu-(Tyr-PO$_3$H$_2$)-Val-Ala-Thr-Arg (SEQ ID No.:1)

The title peptide was synthesized by the stationary-phase synthetic technique using Applied Biosystems automatic peptide synthesizer. Basically this synthesis was carried out by the Boc method [Merrifield, R. B. et al., Adv. Enzymol., 32, 221–298, 1989]. Deprotection was followed by reverse-phase HPLC purification and the agreement with the predicted value was confirmed by amino acid analysis and mass spectrometry.

The other peptides used for immunization of animals and other purposes were also chemically synthesized in the same manner as above.

Example 6

Preparation of an Antibody Specifically Binding to Active-form MAP Kinase

In order that MAP kinase may act as a protein phosphorylase, it is generally considered necessary and sufficient that its two phosphorylation sites ($^{202}$Thr and $^{204}$Tyr in human ERK1 and $^{185}$Thr and $^{187}$Tyr in human ERK2) should be both phosphorylated [Neil G. Anderson et al., Nature, 343, 651–653, 1990]. In order to construct an antibody specifically binding to active-form MAP kinase, the synthetic peptide having the sequence His-Thr-Gly-Phe-Leu-(Thr-PO$_3$H$_2$)-Glu-(Tyr-PO$_3$H$_2$)-Val-Ala-Thr-Arg (SEQ ID NO:1) synthesized in Reference Example 1 was conjugated to BTG with the aid of glutaraldehyde (Wako Pure Chemical) (The above sequence is identical throughout human ERK1, human ERK2, rat ERK1 and ERK2). Rabbits were immunized in the same manner as in Example 5 and the separated sera were purified to give an IgG fraction.

By the same procedure as described in Example 5-(1), the above IgG fraction was applied to a column conjugated to the same synthetic peptide as that used for immunization and the bound fraction was recovered by elution. Then, to remove any antibody that would be binding to phosphorylated tyrosine regardless of amino acid sequence, a column to which phosphorylated tyrosine had been conjugated was prepared and the above recovered fraction was passed through this column and the effluent was collected. This effluent was further passed through a column conjugated to phosphorylated threonine and the effluent fraction was recovered. Finally, it was passed through a column carrying a non-phosphorylated peptide containing the same amino acid sequence as that of the peptide used for immunization, (peptide-2, FIG. 6) (SEQ ID NO:10), and the effluent fraction was recovered and used in the subsequent experiment.

Example 7

Specificity Evaluation of the Antibody Obtained in Example 6

Whether the specificity of the antibody had been improved through the above stages of purification was investigated by the Western blotting technique. The human cell line A-431 (ATCC CRL-1555) was grown in a culture dish (Falcon 3003) containing DMEM supplemented with 10% of fetal calf serum under 5% CO$_2$-air at 37° C. Sixteen

Figure 9:
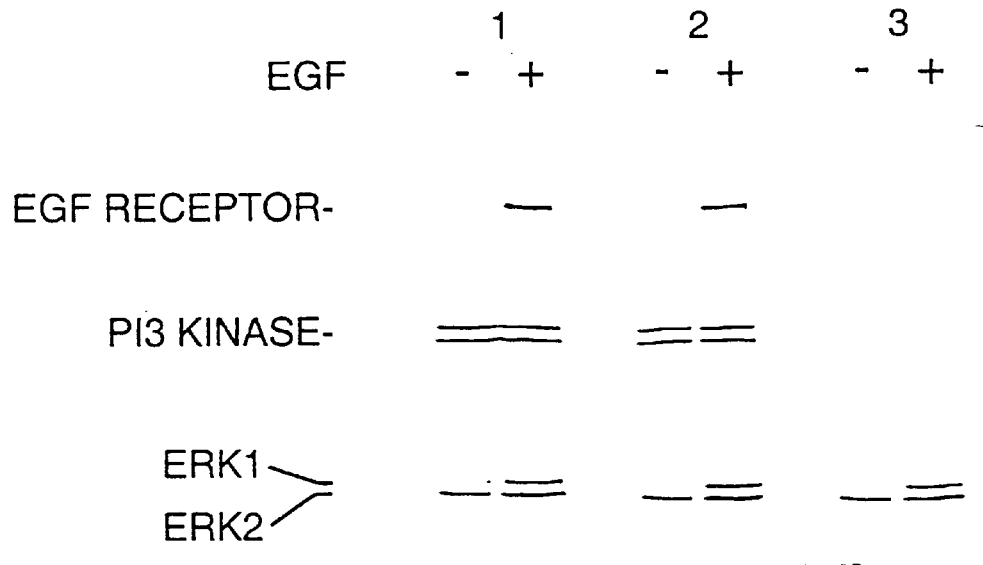
FIG. 9 shows the specificity of the polyclonal antibody against phosphorylated peptides as analyzed by Western blotting in Example 7.

(16) hours after change of medium to serum-free DMEM, human EGF was added at a final concentration of 100 ng/ml and the incubation was continued for 10 minutes. After the medium was discarded, the dish was rinsed with cold PBS (Example 2-(5)) twice and the cells were dissolved by adding 500 μl of electrophoresis solvent (62.5 mM Tris-HCl (pH 6.8), 2% SDS, 5% 2-mercaptoethanol, 10% glycerol). The solution was heated at 95° C. for 5 minutes. This cell solution and a solution prepared from the cells not stimulated with EGF were loaded in parallel on SDS-PAGE of 10% gel concentration and using the antibodies at the various stages of purification, Western blottings was carried out by the same procedure as followed in Example 3-(1) (FIG. 9).

At the stage of IgG down to the stage of affinity purification using the same synthetic peptide as used for immunization, several bands were detected in addition to ERK1 and ERK2. However, with the antibody from which the contaminant binding to phosphorylated tyrosine had been removed, substantially no other bands were found aside from ERK1 and ERK2. Moreover, when the cells were not treated with EGF, ERK1 and ERK2 were detected only as very feeble blots. The above results indicate that an antibody having a sufficiently high specificity for active-form MAP kinase was obtained after the passage through the phosphorylated tyrosine-conjugated column.

Example 8
Sandwich EIA of Active-form Human MAP Kinase ERK1

(1) Biotinylation of the antibody

The purified antibody specific to active-form MAP kinase was biotinylated by the same procedure as described in Example 5-(2).

(2) In vitro activation of MAP kinase

To obtain active-form MAP kinase, the enzyme (MEK; MAP kinase or ERK kinase) which activates MAP kinase by phosphorylation was purified, and using this enzyme, MAP kinase was activated in vitro. The purification was carried out by the procedure reported by Natalie G. Ann et al. [Proc. Natl. Acad. Sci. USA, 90, 5143–5147, 1993].

After the cultured A431 cells were stimulated with EGF for 5 minutes in the same manner as described in Example 7, the dishes were rinsed with 5 ml of ice-cold PBS twice. Then, 0.5 ml/dish of a cell solvent for MAP kinase activity assay (10 mM Tris-HCl pH 7.5, 150 mM NaCl, 2 mM EGTA, 1 mM PMSF, 1 mM $Na_3VO_4$, 0.1 mM $Na_2MoO_4$, 2 mM DTT, 5 mM 2-glycerophosphoric acid, 1 mM NaF, 10 μg/ml leupeptin, 10 μg/ml aprotinin, 1% Triton X-100) was added. The solutions were pooled, sonicated for 30 seconds, and centrifuged at 12000 rpm for 10 minutes, and the supernatant was recovered. The supernatant was diluted 2-fold with buffer S (40 mM HEPES pH 7.4, 2 mM EDTA, 2 mM DTT, 1 mM NaF, 5% glycerol, 0.01% Triton X-100) and applied to a 1 ml SP-Sepharose column (Pharmacia Biotech) equilibrated with the same buffer. Elution was carried out with 3 ml of buffer S containing 0.3M NaCl and the eluate was diluted 5-fold with NaCl-free buffer S. The dilution was applied to a mono Q column (Pharmacia Biotech) equilibrated with the same buffer and the protein was eluted on a NaCl gradient from 0M to 0.3M. Then, a fraction containing MEK protein was specified by Western blotting using an anti-MEK polyconal antibody (Saint Cruz Biotechnology) and used in the subsequent experiment.

The fusion proteins of GST protein and human MAP kinase in the experiment described in Example 3-(2) (GST-human ERK1 protein and GST-human ERK2 protein) were taken, 8 μg each, and respectively activated with the above-described MEK protein in a solution containing 50 mM Tris-HCl pH 7.5, 2 mM EGTA, 10 mM $MgCl_2$, 2 mM NaF, 1 mM DDT, and 200 μM ATP at 37° C.

(3) Establishment of a sandwich EIA system for active-form human MAP kinase ERK1

The monoclonal antibody obtained in Example 2 was diluted with 10 mM carbonate buffer (pH 8.0) at a final concentration of 10 μg/ml and 100 μl/well of the dilution was added to a 96-well immunoplate (Nunc). The plate was allowed to sit at 4° C. overnight to let the antibody immobilized to the solid phase. After the wells were rinsed with PBS twice, 300 μl/well of PBS containing 20% of Block Ace (Snow Brand Milk Products Co.) was added so as to block the surplus binding sites and the plate was stored cold until needed.

Figure 10:
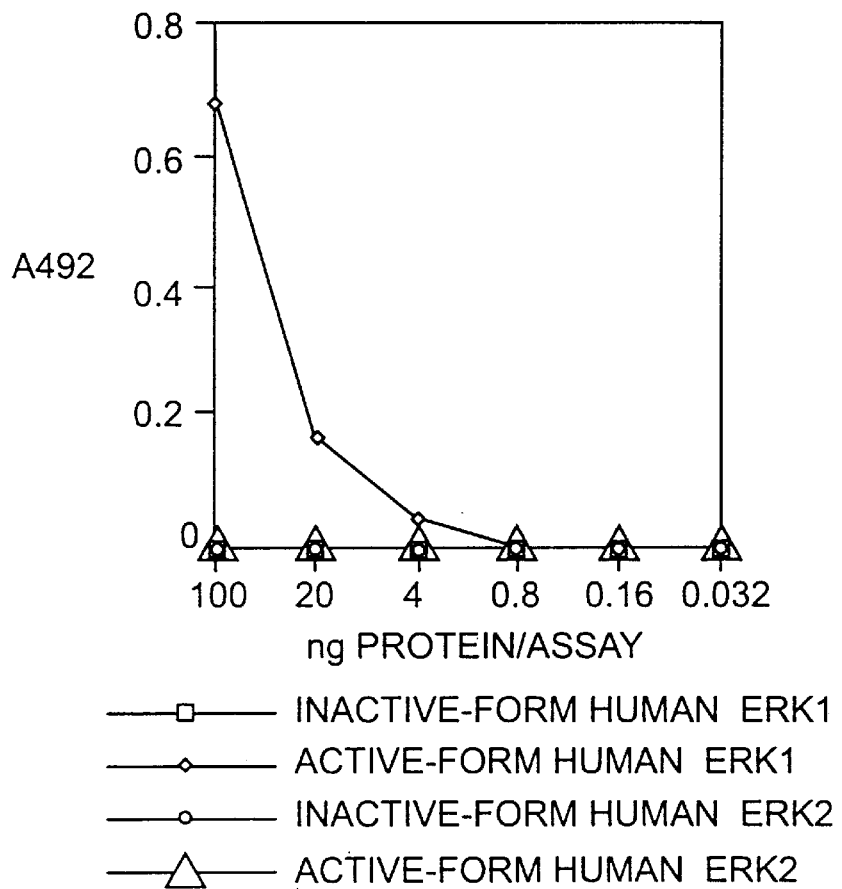
FIG. 10 shows the detection of active-form human MAP kinase ERK1 by the sandwich EIA using anti-human MAP kinase ERK1 monoclonal antibody HE113 and anti-active-form MAP kinase polyclonal antibody as described in Example 8.

The MEK protein-activated GST-human ERK1 protein and GST-human ERK2 protein, as well as the corresponding non-activated fusion proteins, were respectively taken, 0.3 μg each, and each was made up to 75 μl with PBS containing Block Ace. Each of the dilutions was added at 75 μl/well, to a plate which had been washed 3 times with PBS containing 0.05% of Tween 20. Then, using PBS containing Block Ace, a 5-fold dilution series up to 3125 times was prepared and 75 μl aliquots of each dilution were added. The plate was allowed to sit at 4° C. overnight and, then, rinsed 4 times with PBS containing 0.05% of Tween 20. The biotinylated antibody specific for active-form MAP kinase as described in Example 8-(1) was diluted 1000-fold with PBS containing 0.1% of BSA and 100 μl aliquots were added to the wells. The plate was allowed to sit at room temperature for 4 hours, after which the wells were rinsed 4 times with PBS containing 0.05% of Tween 20. Then, a mixture of avidin and biotinylated HRP (both from Vectastain Elite ABC Kit, Vector Laboratories), which had been co-diluted 1000-fold with PBS containing 0.1% of BSA 30 minutes before, were added, 100 μl/well, and the plate was allowed to sit at room temperature for 1 hour. After the wells were rinsed with 6 volumes of PBS containing 0.05% of Tween 20, HRP substrate solution was added so as to carry out the enzymatic reaction in the same manner as Example 2-(3) and the absorbance at 492 nm was measured. It is apparent from the plots of results (FIG. 10) that in the system where the monoclonal antibody HE113 was immobilized to the solid phase, an increase in absorbance occurred only when the active-form human MAP kinase ERK1 was added, while no increase in absorbance was found when inactive-form human MAP kinase ERK1 or human MAP kinase ERK2, whether in active-form or in inactive-form, was added. The results indicated that by employing the above system, active-form human MAP kinase ERK1 can be assayed independently of inactive-form human kinase ERK1, and active and inactive-form human MAP kinase ERK2.

Example 9
Preparation of a MAP Kinase ERK1-specific Polyclonal Antibody and a MAP Kinase ERK2-specific Polyclonal Antibody (1) Preparation of an immunogen and immunization To obtain an antibody specific for MAP kinase ERK1, a couple of peptides having cysteine linked to the N-terminus of peptide-3 [a peptide having the amino acid sequence corresponding to the 283th~300th amino acid residues of human MAP kinase ERK1] (SEQ ID NO:11) and peptide-4 [a peptide having the amino acid sequence corresponding to the 364 to 379th amino acid residues of human MAP kinase ERK1] (SEQ ID NO:12) (FIG. 6), respectively, were synthesized, and using GMBS [N-maleimidobutyryloxysuccinimide; Dojin Kagaku Kenkyusho], each peptide was coupled to BTG (bovine thyroglobulin, Sigma) via the SH group of the cysteine.

To obtain an antibody specific for MAP kinase ERK2, a couple of peptides having cysteine linked to the N-terminus of peptide-5 [a peptide having the amino acid sequence corresponding to the 266 to 283rd amino acid residues of human MAP kinase ERK2] (SEQ ID NO:15) and peptide-6 [a peptide having the amino acid sequence corresponding to the 347 to 360th amino acid residues of human MAP kinase ERK2] (SEQ ID NO:16) (FIG. 11), respectively, were synthesized and, in the same manner as above, each peptide was coupled to BTG.

A rabbit (New Zealand White, male, 2.5 kg) was inoculated subcutaneously with a mixture of the above peptide-BTG complex (containing 0.2 mg of peptide) and Freund's complete adjuvant (Difco Laboratories, USA). Thereafter, the animal was inoculated with a similar mixture with Freund's incomplete adjuvant at 2-week intervals and blood was drawn 1 week after the 4th inoculation to obtain serum.

(2) Purification of the specific antibody

The serum obtained as above was mixed with an equal volume of saturated ammonium sulfate solution and the precipitated protein was centrifugally recovered. The pellet thus obtained was dissolved in PBS (8.1 mM disodium phosphate, 1.5 mM potassium phosphate, 27 mM potassium chloride, 137 mM sodium chloride, pH 7.2) to give a solution of the same volume as the initial serum. This solution was filtered through a 0.22 μm filter (Millipore), diluted 2-fold with 20 mM phosphate buffer (pH 7.0), and loaded on a HiTrap protein G column (Pharmacia Biotech). After the column was washed with 10 ml of 20 mM phosphate buffer (pH 7.0), IgG was eluted with 3 ml of 0.1M glycine-HCl buffer (pH 2.7) and the eluate was neutralized with 150 μl of 1.0M Tris-HCl buffer (pH 9.0).

This IgG fraction was diluted 2-fold with 20 mM phosphate buffer containing 500 mM sodium chloride and loaded on a HiTrap NHS-activated Column (Pharmacia Biotech) carrying the corresponding antigen (peptide) to adsorb the antibody. Elution was carried out with 100 mM glycine-HCl buffer containing 500 mM sodium chloride (pH 2.0) and the eluate was neutralized in the same manner as previously described.

The antibody obtained by using peptide-3 (SEQ ID NO:11) as the antigen was further passed through a peptide-5-conjugated column (SEQ ID NO:15) to remove the ERK2-binding fraction and the effluent fraction was recovered. Similarly the antibody obtained by using peptide-6 (SEQ ID NO:16) as the antigen was passed through a peptide-4-conjugated column (SEQ ID NO:12) to remove the ERK1-binding fraction and the effluent fraction was recovered.

(3) Specificity evaluation of the antigens

The accuracy with which each of anti-peptide-3 antibody and anti-peptide-6 antibody, both prepared as above, differentiates ERK1 from ERK2 or vice versa was evaluated by EIA.

Figure 12A:
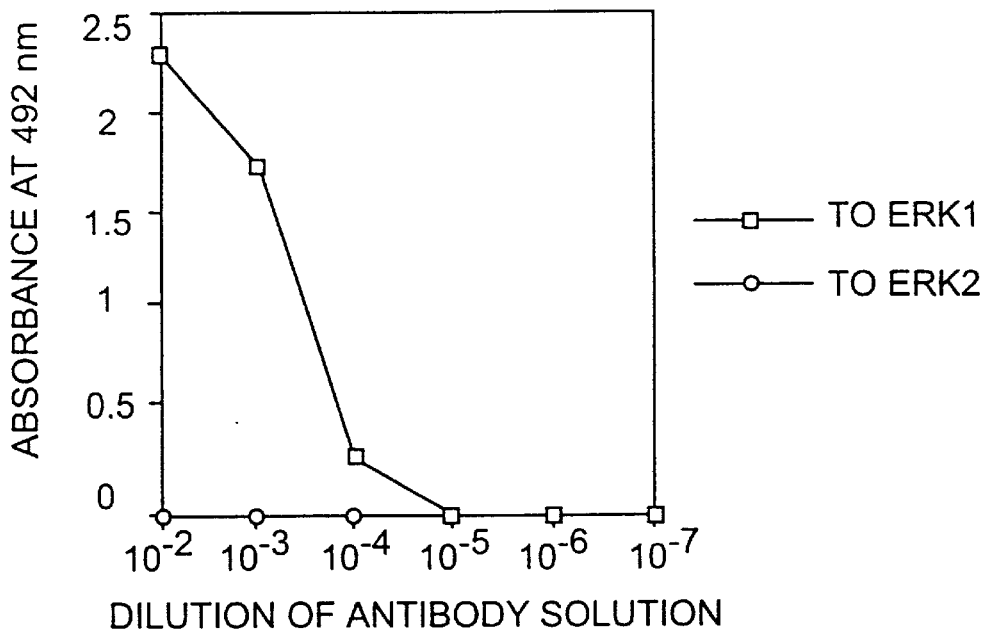
FIG. 12 shows the binding of GST-human ERK1 fusion protein and GST-human ERK2 fused protein by the anti-peptide-3 antibody or anti-peptide-6 antibody of Example 9 in the EIA system.
Figure 12B:
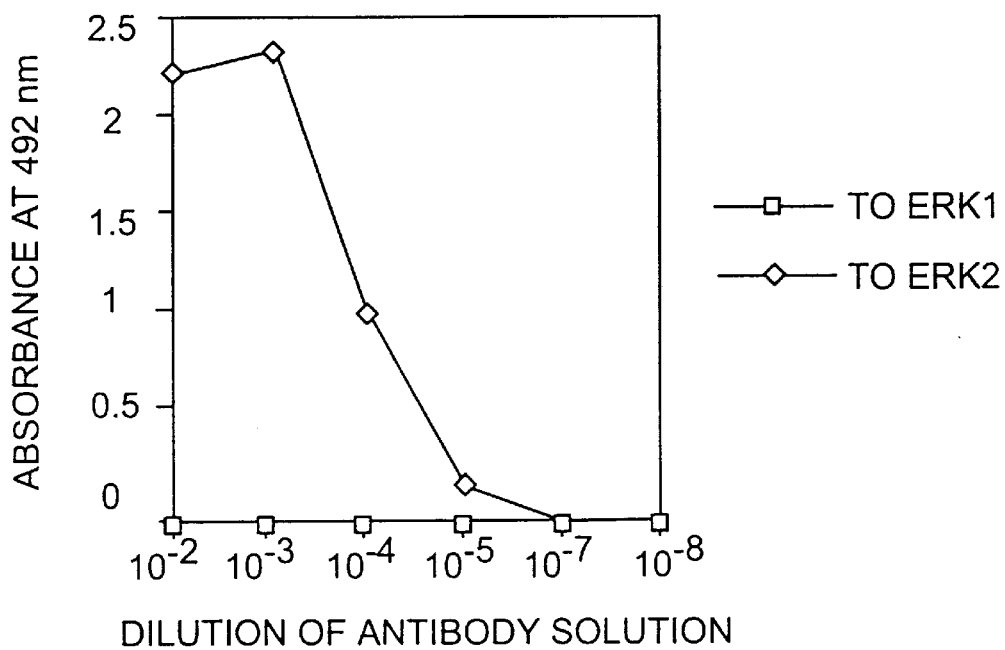

The same procedure as described in Example 3-(2) was followed to assess the specificity of each antibody. As a result, the anti-peptide-3 antibody bound well to GST-human ERK1 protein but did not bind to GST-human ERK2 protein. The anti-peptide-6 antibody bound well to GST-human ERK2 protein but did not bind to GST-human ERK1 protein (FIG. 12). These results indicated that ERK1 and ERK2 can be precisely differentiated by using these antigens.

Example 10

Sandwich Enzyme Immunoassay of MAP Kinase ERK1

(1) Biotinylation of the antibody

The purified anti-peptide-4 antibody was biotinylated in the same manner as described in Example 5-(2).

(2) Establishment of an assay system

The monoclonal antibody HE113 specific for human MAP kinase ERK1, prepared in Example 2, and the polyclonal antibody (anti-peptide-3 antibody) specifically binding to MAP kinase ERK1, prepared in Example 9, were respectively diluted to 20 μg/ml with 10 mM NaHCO$_3$ buffer (pH 8.0) and added to a 96-well EIA plate (Corning, No. 430480), 100 μl per well. Each assay plate was then allowed to sit at 4° C. overnight so as to let the antibody immobilized to the solid phase. After the wells were rinsed twice with PBS (8.1 mM disodium phosphate, 1.5 mM potassium phosphate, 27 mM potassium chloride, 137 mM NaCl, pH 7.2), 300 μl/well of PBS containing 25% of Block Ace (Snow Brand Milk Products Co.) was added and the plate was stored cold until needed.

The plate was washed twice with PBS containing 0.05% of Tween 20 and a concentration series of GST-human ERK1 protein in the same Block Ace-containing PBS as above was added to the plate, 100 μl per well. The plate was then allowed to sit at 4° C. overnight.

Figure 13A:
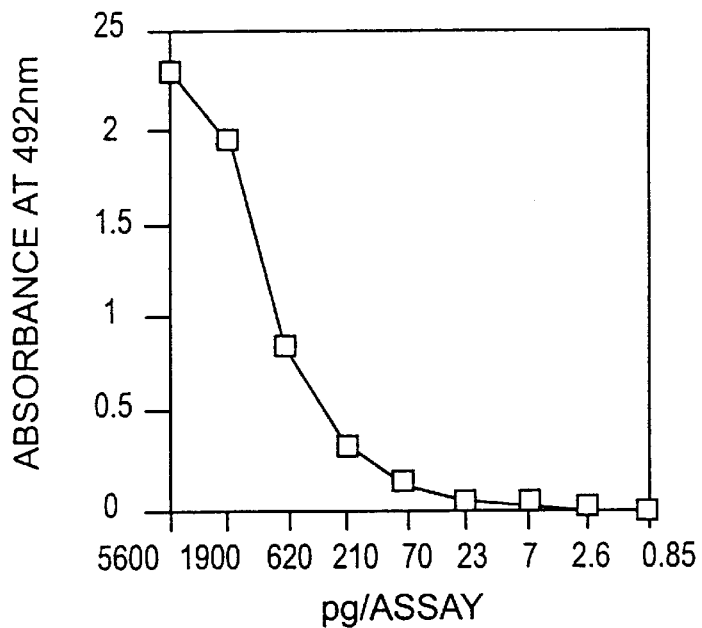
FIG. 13 shows the detection of GST-human MAP kinase ERK1 fusion protein by sandwich EIA in Example 10.
Figure 13B:
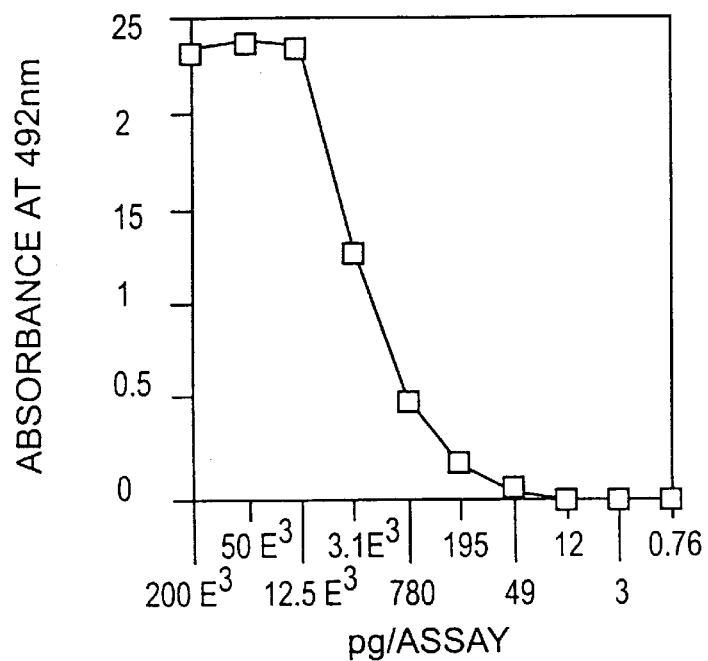

After the wells were rinsed with 3 portions of PBS containing 0.05% of Tween 20, a 1000-fold dilution of the biotinylated anti-peptide-4 antibody in PBS containing 0.1% of BSA was added, 100 μl per well, and the plate was allowed to sit at room temperature for 2 hours. After the wells were rinsed with 4 volumes of PBS containing 0.05% of Tween 20, a mixture of biotinylated horseradish peroxidase (HRP) and avidin [both from Vectastain Elite ABC Kit (Vector Laboratories) diluted 1000-fold], mixed 30 minutes earlier, was added, 100 μl per well, and the plate was allowed to sit at room temperature for 1 hour. The wells were rinsed with 6 volumes of PBS containing 0.05% of Tween 20, after which the HRP substrate solution was added. This enzymatic reaction was carried out as described in Example 2-(3) and the absorbance at 492 nm was measured (FIG. 13). As a result, the detection limit was about 70 pg human ERK1/assay in the system using the monoclonal antibody HE113-immobilized solid phase-and about 50 pg human ERK1/assay in the system using the anti-peptide-3 antibody-immobilized solid phase. In these systems, human MAP kinase ERK2 was not detected, attesting to the high specificity of the antibodies.

Example 11

Sandwich Enzyme Immunoassay of MAP Kinase ERK2

(1) Biotinylation of the antibody

The purified anti-peptide-5 antibody obtained in Example 9 was biotinylated by the same procedure as described in Example 5-(2).

(2) Establishment of an assay system

Figure 14:
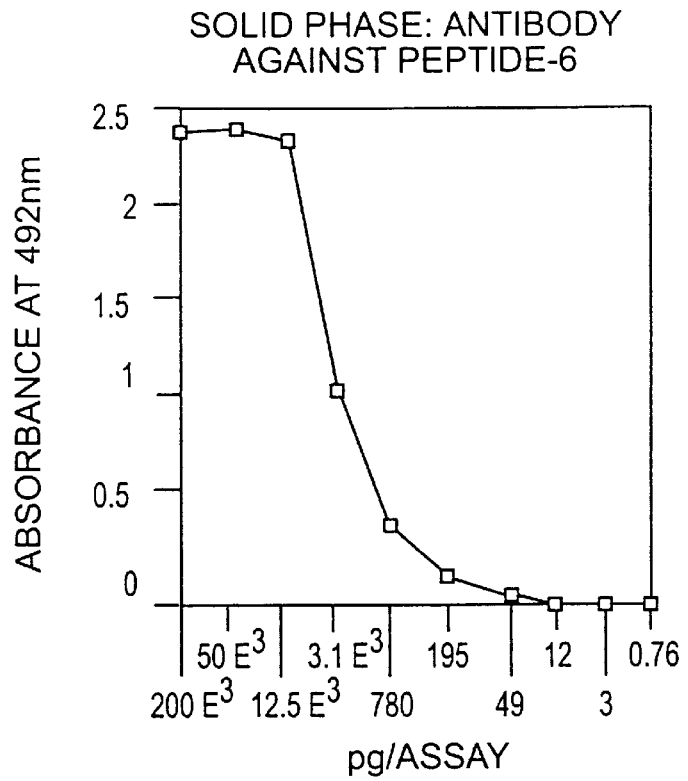
FIG. 14 shows the detection of GST-human MAP kinase ERK2 fusion protein by sandwich EIA in Example 11.

The polyclonal antibody (anti-peptide-6 antibody) specific for MAP kinase ERK2, obtained in Example 9, was immobilized to a 96-well microtiter plate as in Example 10-(2). Then, also in the same manner, a concentration series of GST-human ERK2 protein was added to the wells and assays were carried out with the biotinylated anti-peptide-5 antibody (FIG. 14). As a result, the detection limit was about 50 pg human ERK2/assay. In this system, human MAP kinase ERK1 was not detected, indicating the high specificity of the antibody.

Example 12

Sandwich Enzyme Immunoassay of Active-form MAP kinase ERK1 and active-form MAP kinase ERK2

(1) Biotinylation of the antibody

The polyclonal antibody specific for active-form MAP kinase as constructed in Example 6 was biotinylated by the same procedure as described in Example 5-(2).

(2) In vitro activation of MAP kinase

To prepare an active-form MAP kinase, the enzyme (MEK) which activates MAP kinase by phosphorylation was purified and the MAP kinase was activated using this purified enzyme in vitro. For purification, the procedure reported by Natalie G. Ahn et al. (Proc. Natl. Acad. Sci. USA, 90, 5143–5147, 1993) was followed.

In the same manner as described in Example 7, cultured A431 cells were stimulated with EGF for 5 minutes and the dishes were rinsed with 5 ml of ice-cold PBS twice. Then, a MAP kinase activity assay lysis buffer (10 mM Tris-HCl pH 7.5, 150 mM NaCl, 2 mM EGTA, 1 mM PMSF, 1 mM $Na_3VO_4$, 0.1 mM $Na_2MoO_4$, 2 mM DTT, 5 mM 2-glycerophosphoric acid, 1 mM NaF, 10 μg/ml leupeptin, 10 μg/ml aprotinin, 1% Triton X-100) was added, 0.5 ml per dish. The pooled solution was sonicated for 30 seconds and centrifuged at 12000 rpm for 10 minutes, and the supernatant was recovered. The supernatant was diluted two-fold with buffer S (40 mM HEPES pH 7.4, 2 mM EDTA, 2 mM DTT, 1 mM NaF, 5% glycerol, 0.01% Triton X-100) and loaded on an SP-Sepharose column (Pharmacia Biotech) equilibrated with the same buffer. Elution was carried out with 3 ml of buffer S containing 0.3 M NaCl and the eluate was diluted 5-fold with NaCl-free buffer. This dilution was loaded on a mono Q column (Pharmacia Biotech) equilibrated with the same buffer and the protein was eluted on a gradient of 0M–0.3M NaCl. The eluate was subjected to Western blotting with anti-MEK polyclonal antibody (Saint Cruz Biotechnology) to identify an MEK protein fraction which was used in the subsequent experiment.

The GST protein-human MAP kinase fusion proteins obtained in the experiment described in Example 3-(2), i.e. GST-human ERK1 protein and GST-human ERK2 protein, were respectively taken, 8 μg each, and activated with said MEK protein in a solution containing 50 mM Tris-HCl buffer pH 7.5, 2 mM EGTA, 10 mM $MgCl_2$, 2 mM NaF, 1 mM DTT, 200 μM ATP at 37° C.

(3) Establishment of an EIA system for active-form ERK1 and active-form ERK2.

To assay active-form ERR1, the monoclonal antibody HE113 specific for human ERK1 as described in Example 2 and the anti-peptide-3 antibody specific for human ERK1 as described in Example 9 were respectively diluted with 10 mM carbonate buffer (pH 8.0) to a concentration of 10 μg/ml and the dilutions were respectively added, 100 μl per well, to a 96-well immunoplate (Nunc). Each plate was then allowed to sit at 4° C. overnight to let the antibody immobilized to the solid phase. For the assay of active-form ERK2, the anti-peptide-6 antibody specific for ERK2 as described in Example 9 was coupled to the stationary phase in the same manner as described above. After 2 rinses with PBS, PBS containing 20% of Block Ace (Snow Brand Milk Products Co.) was added, 300 μl per well, to block the surplus binding sites and the plate was stored cold until needed.

The MEK protein-activated GST-human ERK1 protein and GST-human ERK2 protein, as well as the corresponding inactive-form fusion proteins, were respectively taken, 0.3 μg each, and each was diluted to 75 μl with PBS containing 20% of Block Ace. The dilution, 75 μl/well, was added to a plate which had been washed 3 times with PBS containing 0.05% of Tween 20. Then, a series of 5-fold dilutions up to a 3125 fold dilution was prepared using the Block Ace-containing PBS and added to the plate, 75 μl per well.

Figure 15A:
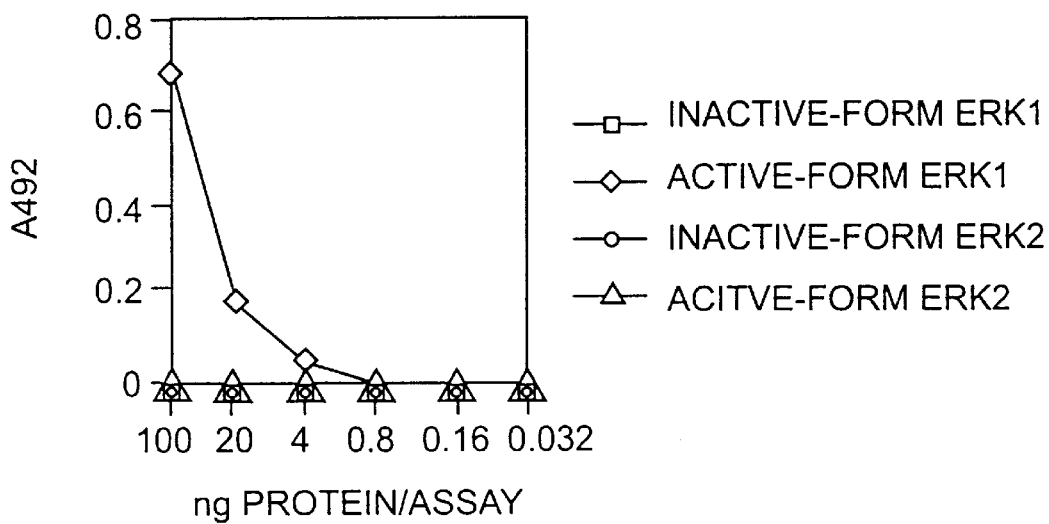
FIG. 15 shows the detection of active-form MAP kinase by sandwich EIA in example 12.
Figure 15B:
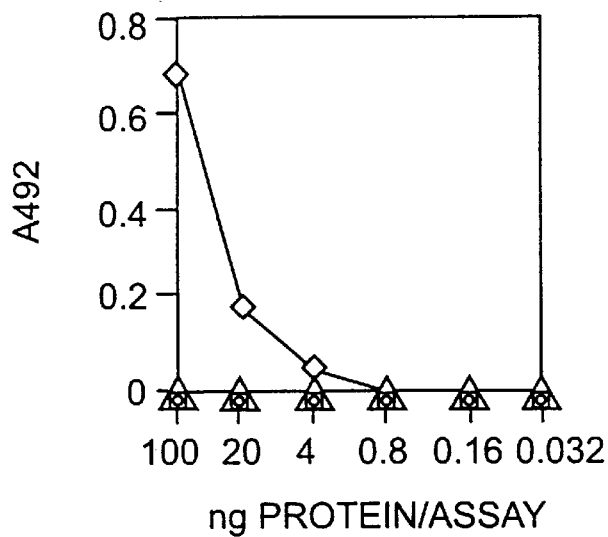
Figure 15C:
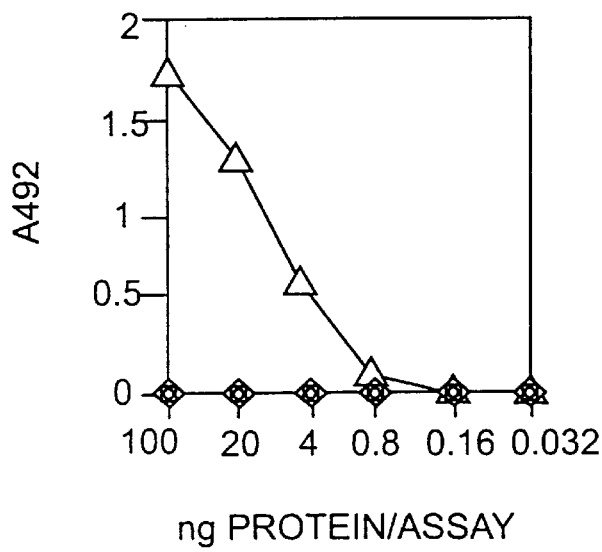

Each plate was allowed to sit at 4° C. overnight and, then, rinsed 4 times with PBS containing 0.05% of Tween 20. The biotinylated antibody specific for active-form MAP kinase as described in Example 12-(1) was diluted 1000-fold with PBS containing 0.1% of BSA and added to the plate, 100 μl per well. The plate was allowed to sit at room temperature for 4 hours, after which it was rinsed 4 times with PBS containing 0.05% of Tween 20. Then, a 1000-fold dilution mixture of avidin and biotinylated HRP (both from Vectastain Elite ABC Kit, Vector Laboratories), which had been prepared using 0.1% BSA/PBS 30 minutes before, was added to the plate, 100 μl per well, and the plate was allowed to sit at room temperature for 1 hour. After the wells were rinsed with 6 volumes of PBS containing 0.05% of Tween 20, the HRP substrate solution was added for enzymatic reaction as in Example 2-(3) and the absorbance was measured at 492 nm. It is apparent from the plots of results (FIG. 15) that in the system using monoclonal antibody HE113 or anti-peptide-3 antibody as immobilized to a solid phase, an increase in absorbance was found only when activated GST-human ERK1 protein was added and no increase occurred when non-activated GST-human ERK1 protein was added or GST-human ERK2 protein, whether activated or non-activated, was added. On the other hand, in the system using the anti-peptide-6 antibody immobilized to a solid phase, an increase in absorbance occurred only when activated GST-human ERK2 protein was added and no increase was found when non-activated GST-human ERK2 protein was added or GST-human ERK1 protein, whether activated or non-activated, was added. The above results indicated the capability of the system to assay active-form MAP kinase, discriminating ERK1 from ERK2 or vice versa.

Example 13

Detection Limit Evaluation of the Assay System Described in Example 12

Since the MAP kinase used in Example 12 was a mixture of the active-form and the inactive form, the detection limit of the assay systems could not be established. Therefore, using the antibody obtained in Example 6, the purification of active-form MAP kinase was carried out and the detection limit was investigated.

(1) Purification of active-form MAP kinase

The antibody (1.7 mg) specific for active-form MAP kinase as obtained in Example 6 was conjugated to a HiTrap NHS-activated Column (Pharmacia Biotech). The active-form MAP kinase obtained in Example 12-(2) (GST-ERK1 fusion protein or GST-ERK2 fusion protein) was diluted 5-fold with 20 mM phosphate buffer (pH 7.0) containing 0.5M NaCl and 0.05% Tween-20 and the dilution was applied to the column. The effluent fraction was applied to the column again. The column was then washed with 5 ml of the same buffer as used for dilution and the protein was eluted with 5 ml of 0.1M glycine-HCl buffer (pH 2.0) containing 0.5M NaCl and 0.05% Tween-20 and the eluate was neutralized with 250 μl of 1M Tris-HCl buffer (pH 9.0). The neutralized eluate was then diluted 3-fold with 20 mM phosphate buffer (pH 7.0) containing 0.05% Tween-20 and blended with 100 μl of glutathione-Sepharose 4B (Pharmacia Biotech) at 4° C. for 1 hour. The glutathione-Sepharose 4B was centrifugally collected and washed with PBS, and 0.5 ml of 50 mM Tris-HCl buffer (pH 8.0) containing 10 mM glutathione and 0.05% Tween-20 was added, whereby the protein was recovered from the glutathione-Sepharose 4B.

(2) Detection limit study

A portion of the above active-form MAP kinase solution was subjected to protein assay in the system described in Example 10 or 11. Then, using this active-form MAP kinase solution of known protein content, assays were carried out

Figure 16A:
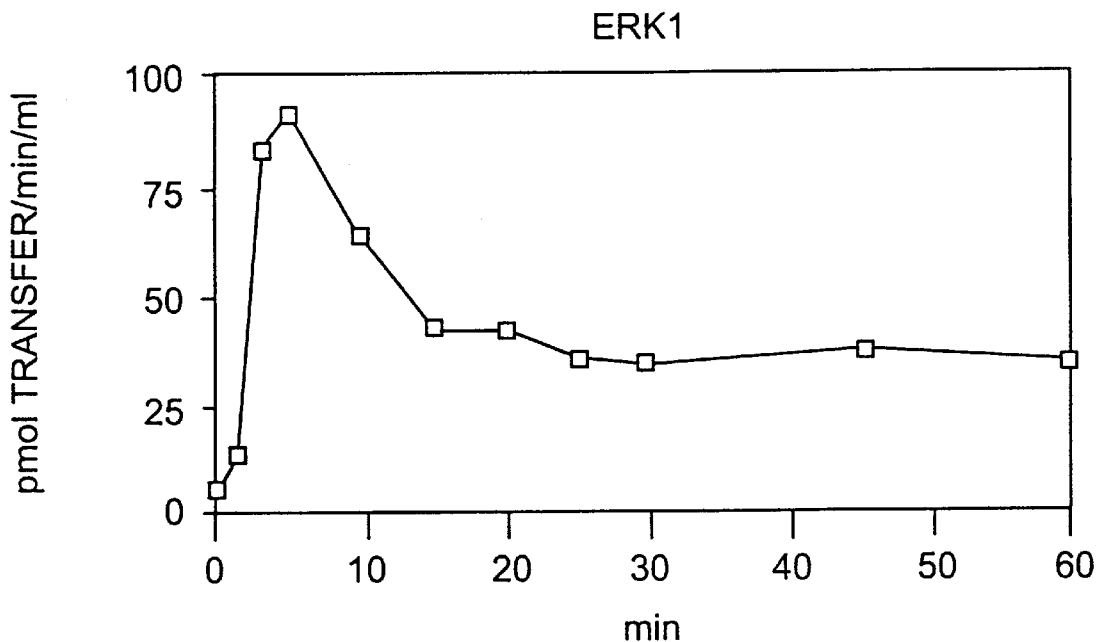
FIG. 16 shows the sandwich EIA analysis of the changes in MAP kinase ERK1 activity and MAP kinase ERK2 activity due to NGF stimulation of PC-12 cells as described in Example 14.
Figure 16B:
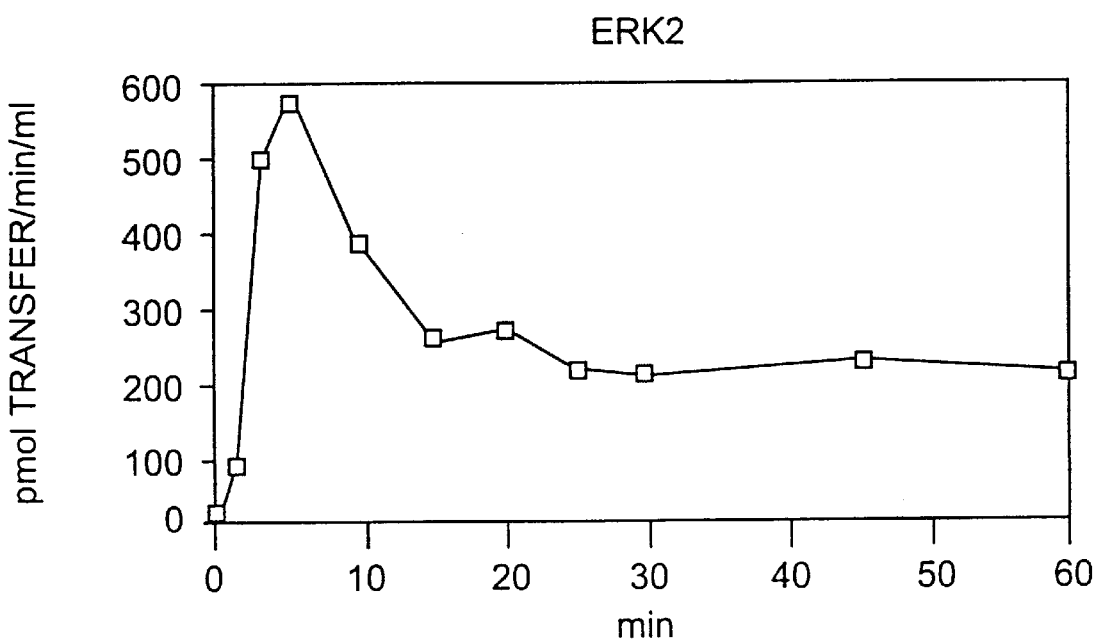

Example 14
The Detection by Enzyme Immunoassay of the Change of MAP Kinase Activity as Induced by NGF Stimulation of Cultured PC-12 Cells Using 10% fetal calf serum-DMEM as the medium, the rat-derived cultured cell line PC-12 (Adrenal pheochromocytoma ATCC CRL-1721) was seeded in 6 cm dishes (Falcon 3002), $2.8 \times 10^6$ cells per dish, and grown under 5% $CO_2$ at 37° C. overnight. After the medium was changed to serum-free medium, the cells were further grown for 1 hour. The medium was then replaced with DMEM containing 100 ng/ml of NGF and 0.1% of BSA and the cells were further grown for a series of time periods. In each case, the medium was discarded and the cells were rinsed with ice-cold PBS twice. Then, the MAP kinase activity assay lysis buffer described in Example 12-(2) was added, 250 μl per dish, and the lysed cells were transferred to an Eppendorf tube. This lysate was allowed to stand on ice for 5 minutes and, then, centrifuged at 16000×g for 5 minutes to recover the supernatant. The active-form MAP kinase ERK1 and active-form MAP kinase ERK2 in this supernatant were quantitated in the enzyme immunoassay system described in Example 12. Moreover, the phosphorylase activity of the MAP kinase ERK1 and MAP kinase ERK2 activated in vitro in Example 12-(2) was assayed by the method of Tadayo Miyasaka et al. [J. Biol. Chem., 265, 4730–4735, 1990], and this enzyme of known activity and said PC-12 lysate were co-assayed by enzyme immunoassay. Comparing the values found, the absorbance value was converted to the phosphorylase activity value. The results are shown in FIG. 16. It is clear from the results that the change of MAP kinase activity by NGF stimulation of PC-12 could be quantitated for both MAP kinase ERK1 and MAP kinase ERK2 by utilizing the system described in Example 12. This activation pattern is in good agreement with the findings reported by Gotoh Y. et al., Eur. J. Biochem, 193, 661–669, 1990. Therefore, it is also clear that the assay system of Example 12 can be successfully applied to rat MAP kinase ERK1 and MAP kinase ERK2.

The monoclonal antibody of the present invention binds to human MAP kinase ERK1 with high sensitivity and high binding affinity and, therefore, can be used with advantage as a reagent for the detection or assay of human MAP kinase ERK1 of various cell origins. This means that, with this antibody, the expression of human MAP kinase ERK1 and its distribution in cells and tissues can be explored. The anti-ERK1 antibody and anti-ERK2 antibody of the present invention bind to the corresponding species of MAP kinase with high sensitivity and high affinity and, therefore, can be used with advantage as reagents for the detection or assay of the respective types of MAP kinase. Furthermore, the active-form MAP kinase antibody (anti-phosphorylated peptide antibody) of the present invention binds to active-form MAP kinase with high sensitivity and good affinity so that by utilizing this antibody, the detection or assay of active-form MAP kinase of various cell origins, that is to say the detection or assay of MAP kinase activity, can be successfully carried out without resort to, for example, radioactive reagents. In addition, by using the antibodies specific for various types of MAP kinase according to the invention in a suitable combination, the activity of any given species of MAP kinase can be detected or assayed with high sensitivity to the exclusion of other species of MAP kinase. In this manner, the distribution and level of expression of any species of MAP kinase and stimulus-induced changes in its activity in cells and tissues can be explored and, hence, the role of each species of MAP kinase in vivo can be further elucidated.

Also, these methods of detection or assay can be used to diagnose various MAP kinase-related diseases, serving well for such purposes as choosing appropriate therapies and identifying pathologic causes. They can also be used to elucidate the mechanisms of action of various drugs.

What is claimed is:

1. A method for detecting the active-form of ERK2 MAP kinase which comprises:
   a) contacting a sample with a first anti-MAP kinase antibody that specifically binds to the peptide sequence His-Thr-Gly-Phe-Leu-(Thr-$PO_3H_2$)-Glu-(Tyr-$PO_3H_2$)-Val-Ala-Thr-Arg (SEQ ID NO. 1), and to a second anti-MAP kinase antibody that specifically binds to an ERK2 sequence selected from the group consisting of Ser-Leu-Pro-His-Lys-Asn-Lys-Val-Pro-Trp-Asn-Arg-Leu-Phe-Pro-Asn-Ala-Asp (SEQ ID NO. 15) and Ile-Phe-Glu-Glu-Thr-Ala-Arg-Phe-Gln-Pro-Gly-Tyr-Arg-Ser (SEQ ID NO. 16), and
   b) detecting the active-form ERK2 which specifically binds to both antibodies.

2. The method of claim 1 wherein said active-form of ERK2 specifically bound to both antibodies is detected by detecting a label bound to one or both anti-MAP kinase antibodies, or to a secondary antibody which binds to one or both anti-MAP kinase antibodies, wherein said label is selected from the group consisting of radioisotopes, enzymes, fluorescent or chemiluminescent labels.

3. The method of claim 1 wherein the active-form of ERK2 MAP kinase to be detected comprises a mutein of the ERK2 MAP kinase,
   wherein said mutein is the result of addition, deletion, and/or substitution of amino acids of ERK2 MAP kinase, and
   wherein said mutein can bind to antibodies which specifically bind to the peptide sequence His-Thr-Gly-Phe-Leu-(Thr-$PO_3H_2$)-Glu-(Tyr-$PO_3H_2$)-Val-Ala-Thr-Arg (SEQ ID NO. 1), and to antibodies which specifically bind to a peptide sequence selected from the group consisting of Ser-Leu-Pro-His-Lys-Asn-Lys-Val-Pro-Trp-Asn-Arg-Leu-Phe-Pro-Asn-Ala-Asp (SEQ ID NO. 15) and Ile-Phe-Glu-Glu-Thr-Ala-Arg-Phe-Gln-Pro-Gly-Tyr-Arg-Ser (SEQ ID NO. 16).

4. A method for detecting the active-form of ERK2 MAP kinase as claimed in any of claims 1, or 2 or 3, said method being an enzyme immunoassay method.

5. The method for detecting the active-form of ERK2 MAP kinase as claimed in claim 4, wherein said immunoassay comprises a sandwich immunoassy technique.

6. A method for quantitating the active-form of ERK2 MAP kinase which comprises:
   a) contacting a sample with a first anti-MAP kinase antibody that specifically binds to the peptide sequence His-Thr-Gly-Phe-Leu-(Thr-$PO_3H_2$)-Glu-(Tyr-$PO_3H_2$)-Val-Ala-Thr-Arg (SEQ ID NO. 1), and with a seconrd antibody that specifically binds to an ERK2 sequence selected from the group consisting of Ser-Leu-Pro-His-Lys-Asn-Lys-Val-Pro-Trp-Asn-Arg-Leu-Phe-Pro-Asn-Ala-Asp (SEQ ID NO. 15) and Ile-Phe-Glu-Glu-Thr-Ala-Arg-Phe-Gln-Pro-Gly-Tyr-Arg-Ser (SEQ ID NO. 16), and
   b) quantitating the active-form ERK2 which specifically binds to both antibodies.

7. The method of claim 6 wherein said active-form of ERK2 specifically bound to both antibodies is detected by detecting a label bound to one or both anti-MAP kinase antibodies, or to a secondary antibody which binds to one or both anti-MAP kinase antibodies, wherein said label is selected from the group consisting of radioisotopes, enzymes, fluorescent or chemiluminescent labels.

8. The method of claim 6 wherein the active-form of ERK2 MAP kinase to be detected comprises a mutein of the ERK2 MAP kinase,
   wherein said mutein is the result of addition, deletion, and/or substitution of amino acids of ERK2 MAP kinase, and
   wherein sasid mutein can bind to antibodies which specifically bind to the peptide seguence His-Thr-Gly-Phe-Leu-(Thr-$PO_3H_2$)-Glu-(Tyr-$PO_3H_2$)-Val-Ala-Thr-Arg (SEQ ID NO. 1), and to antibodies which specifically bind to a peptide sequence selected from the group consisting of Ser-Leu-Pro-His-Lys-Asn-Lys-Val-Pro-Trp-Asn-Arg-Leu-Phe-Pro-Asn-Ala-Asp (SEQ ID NO. 15) and Ile-Phe-Glu-Glu-Thr-Ala-Arg-Phe-Gln-Pro-Gly-Tyr-Arg-Ser (SEQ ID NO. 16).

9. A method for quantitating the active-form of ERK2 MAP kinase as claimed in any of claims 6, or 7 or 8, said method being an enzyme immunoassay method.

10. The method for assaying the active-form of ERK2 MAP kinase as claimed in claim 9, wherein said immunoassay comprises a sandwich immunoassay technique.

11. A method for determining an association of the level and activity of ERK2 MAP kinase in a patient specimen with a disease state comprising:
    a) quantitating the active-form of ERK2 MAP kinase in the specimen by the method of claim 6,
    b) quantitating the level of ERK2 MAP kinase in the specimen,
    c) comparing the level and activity of ERK2 MAP kinase in the patient specimen to the level and activity of ERK2 MAP kinase in a normal specimen, and
    d) detecting a correlation between the level and activity of ERK2 MAP kinase in a patient and a disease state.

12. A composition comprising:
    a first anti-MAP kinase antibody that specifically bind to the peptide sequence His-Thr-Gly-Phe-Leu-(Thr-$PO_3H_2$)-Glu-(Tyr-$PO_3H_2$)-Val-Ala-Thr-Arg (SEQ ID NO. 1), and
    a second anti-MAP kinase antibody that specifically binds to the amino acid sequence Ser-Leu-Pro-His-Lys-Asn-Lys-Val-Pro-Trp-Asn-Arg-Leu-Phe-Pro-Asn-Ala-Asp (SEQ ID NO. 15).

13. A composition comprising:
    a first anti-MAP kinase antibody that specifically binds to the peptide sequence His-Thr-Gly-Phe-Leu-(Thr-$PO_3H_2$)-Glu-(Tyr-$PO_3H_2$)-Val-Ala-Thr-Arg (SEQ ID NO. 1), and a second anti-MAP kinase antibody that specifically binds to the amino acid sequence Ile-Phe-Glu-Glu-Thr-Ala-Arg-Phe-Gln-Pro-Gly-Tyr-Arg-Ser (SEQ ID NO. 16).

14. The composition of claim 12 or 13, further comprising a label bound to one or both anti-MAP kinase antibodies, or to a secondary antibody which binds to one or both anti-MAP kinase antibodies, wherein said label is selected from the group consisting of radioisotopes, enzymes, fluorescent or chemiluminescent labels.

* * * * *